US009055979B2

(12) United States Patent
Alcock et al.

(10) Patent No.: US 9,055,979 B2
(45) Date of Patent: Jun. 16, 2015

(54) CORD FOR VERTEBRAL FIXATION HAVING MULTIPLE STIFFNESS PHASES

(75) Inventors: Ben Alcock, Winterthur (CH); Thomas Nydegger, Thalwil (CH)

(73) Assignee: Zimmer GMBH, Winterthur (CH)

( * ) Notice: Subject to any disclaimer, the term of this patent is extended or adjusted under 35 U.S.C. 154(b) by 1653 days.

(21) Appl. No.: 12/327,710

(22) Filed: Dec. 3, 2008

(65) Prior Publication Data
US 2010/0137912 A1 Jun. 3, 2010

(51) Int. Cl.
*A61B 17/70* (2006.01)

(52) U.S. Cl.
CPC ......... *A61B 17/7022* (2013.01); *A61B 17/7008* (2013.01)

(58) Field of Classification Search
CPC ........... A61B 17/7014; A61B 17/7019; A61B 17/702; A61B 17/7022; A61B 17/7026; A61B 17/7031
USPC ............................. 606/61, 246–279, 300–321
See application file for complete search history.

(56) References Cited

U.S. PATENT DOCUMENTS

| 4,743,260 | A | 5/1988 | Burton |
| 5,176,708 | A | 1/1993 | Frey et al. |
| 5,375,823 | A | 12/1994 | Navas |
| 5,540,688 | A | 7/1996 | Navas |
| 5,562,660 | A | 10/1996 | Grob |
| 5,725,582 | A | 3/1998 | Bevan et al. |
| 5,782,831 | A | 7/1998 | Sherman et al. |
| RE36,221 | E | 6/1999 | Breard et al. |
| 6,248,106 | B1 | 6/2001 | Ferree |
| 6,290,700 | B1 | 9/2001 | Schmotzer |
| 6,610,079 | B1 | 8/2003 | Li et al. |
| 6,802,844 | B2 | 10/2004 | Ferree |
| 6,986,771 | B2 | 1/2006 | Paul et al. |
| 6,989,011 | B2 | 1/2006 | Paul et al. |
| 7,008,424 | B2 | 3/2006 | Teitelbaum |
| 7,029,475 | B2 | 4/2006 | Panjabi |
| 7,137,985 | B2 | 11/2006 | Jahng |

(Continued)

FOREIGN PATENT DOCUMENTS

| EP | 0516567 A1 | 12/1992 |
| EP | 0669109 A1 | 8/1995 |

(Continued)

OTHER PUBLICATIONS

Davis, Regmald J. and Maxwell, James H., "Dynesys LIS surgical technique," Dynesys LIS Less Invasive Surgery, The Dynamic Stabilization System, 2005, Zimmer SPine, Inc., 24 pgs.

*Primary Examiner* — Eduardo C. Robert
*Assistant Examiner* — Christina Negrellirodrigue
(74) *Attorney, Agent, or Firm* — Seager, Tufte & Wickhem LLC

(57) ABSTRACT

A dynamic stabilization system for stabilizing a vertebral segment of a spine. The system includes a first vertebral anchor, a second vertebral anchor and a cord. The system may also include a spacer positioned between the first and second vertebral anchor through which the cord extends. The first vertebral anchor is configured to be secured to a first vertebra and the second vertebral anchor is configured to be secured to a second vertebra. The cord is extendable from the first vertebral anchor to the second vertebral anchor. The cord has a variable stiffness through a range of displacement, wherein the stiffness of the cord increases as an applied tensile force on the cord is increased.

14 Claims, 23 Drawing Sheets

(56) References Cited

U.S. PATENT DOCUMENTS

| | | |
|---|---|---|
| 7,326,210 B2 | 2/2008 | Jahng et al. |
| 2002/0035366 A1 | 3/2002 | Walder et al. |
| 2004/0049189 A1 | 3/2004 | Le Couedic et al. |
| 2004/0215191 A1 | 10/2004 | Kitchen |
| 2004/0225289 A1 | 11/2004 | Bierdermann et al. |
| 2005/0010220 A1 | 1/2005 | Casutt et al. |
| 2005/0056979 A1 | 3/2005 | Studer et al. |
| 2005/0065516 A1 | 3/2005 | Jahng |
| 2005/0085815 A1 | 4/2005 | Harms et al. |
| 2005/0096652 A1 | 5/2005 | Burton |
| 2005/0124991 A1 | 6/2005 | Jahng |
| 2005/0143737 A1 | 6/2005 | Pafford et al. |
| 2005/0154390 A1 | 7/2005 | Bierdermann et al. |
| 2005/0177157 A1 | 8/2005 | Jahng |
| 2005/0203511 A1 | 9/2005 | Wilson-MacDonald et al. |
| 2005/0203513 A1 | 9/2005 | Jahng et al. |
| 2005/0203514 A1 | 9/2005 | Jahng et al. |
| 2005/0203517 A1 | 9/2005 | Jahng et al. |
| 2005/0277922 A1 | 12/2005 | Trieu et al. |
| 2006/0106380 A1 | 5/2006 | Colleran |
| 2006/0111715 A1 | 5/2006 | Jackson |
| 2006/0142758 A1 | 6/2006 | Petit |
| 2006/0173454 A1 | 8/2006 | Spitler et al. |
| 2006/0195093 A1 | 8/2006 | Jahng |
| 2006/0200129 A1 | 9/2006 | Denti |
| 2006/0212033 A1 | 9/2006 | Rothman et al. |
| 2006/0229615 A1 | 10/2006 | Abdou |
| 2006/0247638 A1 | 11/2006 | Trieu et al. |
| 2007/0005062 A1 | 1/2007 | Lange et al. |
| 2007/0005063 A1 | 1/2007 | Bruneau et al. |
| 2007/0016200 A1 | 1/2007 | Jackson |
| 2007/0055244 A1 | 3/2007 | Jackson |
| 2007/0100341 A1 | 5/2007 | Reglos et al. |
| 2007/0118119 A1 | 5/2007 | Hestad |
| 2007/0129729 A1 | 6/2007 | Petit et al. |
| 2007/0198088 A1 | 8/2007 | Biedermann et al. |
| 2007/0225710 A1 | 9/2007 | Jahng et al. |
| 2007/0233075 A1 | 10/2007 | Dawson |
| 2007/0233087 A1 | 10/2007 | Schlapfer |
| 2007/0233095 A1 | 10/2007 | Schlaepfer |
| 2007/0239158 A1 | 10/2007 | Trieu et al. |
| 2007/0270821 A1* | 11/2007 | Trieu et al. ............... 606/61 |
| 2007/0270860 A1 | 11/2007 | Jackson |
| 2007/0293862 A1 | 12/2007 | Jackson |
| 2008/0009863 A1 | 1/2008 | Bond et al. |
| 2008/0021459 A1 | 1/2008 | Lim |
| 2008/0021465 A1 | 1/2008 | Shadduck et al. |
| 2008/0039843 A1 | 2/2008 | Abdou |
| 2008/0091213 A1 | 4/2008 | Jackson |
| 2008/0140076 A1 | 6/2008 | Jackson |
| 2008/0147122 A1 | 6/2008 | Jackson |
| 2008/0161857 A1 | 7/2008 | Hestad et al. |
| 2008/0177317 A1 | 7/2008 | Jackson |
| 2008/0177388 A1 | 7/2008 | Patterson et al. |
| 2008/0183216 A1 | 7/2008 | Jackson |
| 2008/0195153 A1 | 8/2008 | Thompson |
| 2008/0234737 A1 | 9/2008 | Boschert |
| 2008/0234738 A1 | 9/2008 | Zylber et al. |
| 2008/0234744 A1 | 9/2008 | Zylber et al. |
| 2008/0262551 A1 | 10/2008 | Rice et al. |
| 2008/0275456 A1 | 11/2008 | Vonwiller et al. |
| 2008/0294198 A1 | 11/2008 | Jackson |
| 2008/0300633 A1 | 12/2008 | Jackson |
| 2008/0319486 A1 | 12/2008 | Hestad et al. |
| 2009/0005817 A1 | 1/2009 | Friedrich et al. |
| 2009/0012562 A1 | 1/2009 | Hestad et al. |
| 2009/0036924 A1 | 2/2009 | Egli et al. |
| 2009/0082815 A1 | 3/2009 | Zylber et al. |
| 2009/0093846 A1 | 4/2009 | Hestad |
| 2009/0099606 A1 | 4/2009 | Hestad et al. |

FOREIGN PATENT DOCUMENTS

| | | |
|---|---|---|
| EP | 0669109 B1 | 8/1995 |
| EP | 1523949 A1 | 4/2005 |
| EP | 1523949 B1 | 4/2005 |
| EP | 1719468 A1 | 11/2006 |
| FR | 2715057 A1 | 7/1995 |
| FR | 2775583 A1 | 9/1999 |
| FR | 2844180 A1 | 3/2004 |
| FR | 2867057 A1 | 9/2005 |
| NL | 7610576 | 3/1978 |
| WO | 9519149 | 7/1995 |
| WO | 9905980 A1 | 2/1999 |
| WO | 9944527 A1 | 9/1999 |
| WO | 2004024011 A1 | 3/2004 |
| WO | 2004089244 A2 | 10/2004 |
| WO | 2005037110 A2 | 4/2005 |
| WO | 2005037150 A1 | 4/2005 |
| WO | 2005087121 A1 | 9/2005 |
| WO | 2006066685 A1 | 6/2006 |
| WO | 2007044795 A2 | 4/2007 |
| WO | 2007087476 A1 | 8/2007 |
| WO | 2008006098 A2 | 1/2008 |
| WO | 2008013892 A2 | 1/2008 |
| WO | 2008021319 A2 | 2/2008 |
| WO | 2008034130 A2 | 3/2008 |
| WO | 2008067200 A1 | 6/2008 |
| WO | 2008134703 A2 | 11/2008 |

* cited by examiner

CORD FOR VERTEBRAL FIXATION HAVING MULTIPLE STIFFNESS PHASES

TECHNICAL FIELD

The disclosure is directed to a vertebral stabilization system. More particularly, the disclosure is directed to a cord for use in a vertebral stabilization system having multiple phases of stiffness.

BACKGROUND

The spinal column of a patient includes a plurality of vertebrae linked to one another by facet joints, ligaments and an intervertebral disc located between adjacent vertebrae. The facet joints, ligaments and intervertebral disc allow one vertebra to move relative to an adjacent vertebra, providing the spinal column a range of motion. Diseased, degenerated, damaged, or otherwise impaired facet joints, ligaments and/or intervertebral discs may cause the patient to experience pain or discomfort and/or loss of motion, thus prompting surgery to alleviate the pain and/or restore motion of the spinal column.

Accordingly, there is an ongoing need to provide alternative devices, assemblies, systems and/or methods that can function to alleviate pain or discomfort, provide stability, such as dynamic stability, and/or restore a range of motion to a spinal segment of a spinal column. It may be desirable that such apparatus replicate and/or approximate the functionality characteristics of a natural spinal segment.

SUMMARY

The disclosure is directed to several alternative designs, materials and methods of manufacturing medical device structures and assemblies.

Accordingly, one illustrative embodiment is a dynamic stabilization system for stabilizing a vertebral segment of a spine. The system includes a first vertebral anchor, a second vertebral anchor and a cord. The first vertebral anchor is configured to be secured to a first vertebra and the second vertebral anchor is configured to be secured to a second vertebra. The cord is extendable from the first vertebral anchor to the second vertebral anchor. The cord has a variable stiffness through a range of displacement, wherein the stiffness of the cord increases as an applied tensile force on the cord is increased.

Another illustrative embodiment is a dynamic stabilization system for stabilizing a vertebral segment of a spine. The system includes a first vertebral anchor configured to be secured to a first vertebra, a second vertebral anchor configured to be secured to a second vertebra, and a cord extendable between the first vertebral anchor and the second vertebral anchor. The cord has a first phase of stiffness when subjected to a first range of tensile loading, a second phase of stiffness when subjected to a second range of tensile loading greater than the first range of tensile loading, and a third phase of stiffness when subjected to a third range of tensile loading greater than the second range of tensile loading.

Another illustrative embodiment is a dynamic stabilization system for stabilizing a vertebral segment of a spine. The system includes a first vertebral anchor, a second vertebral anchor, a spacer and a cord. The first vertebral anchor is configured to be secured to a first vertebra. The second vertebral anchor is configured to be secured to a second vertebra. The spacer is positionable between the first vertebral anchor and the second vertebral anchor. The cord is sized for insertion through the spacer and is extendable from the first vertebral anchor to the second vertebral anchor. The cord includes a means for varying the stiffness of the cord dependent of a tensile load applied to the cord.

Yet another illustrative embodiment is a method of stabilizing a vertebral segment of a spine. The method includes providing a first vertebral anchor secured to a first vertebra, a second vertebral anchor secured to a second vertebra, and a cord extending between the first vertebral anchor and the second vertebral anchor. The cord is elongated to a first elongated length, wherein at the first elongated length the cord has a first stiffness. The cord is further elongated to a second elongated length greater than the first elongated length, wherein at the second elongated length the cord has a second stiffness different from the first stiffness.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which.

Figure 1:
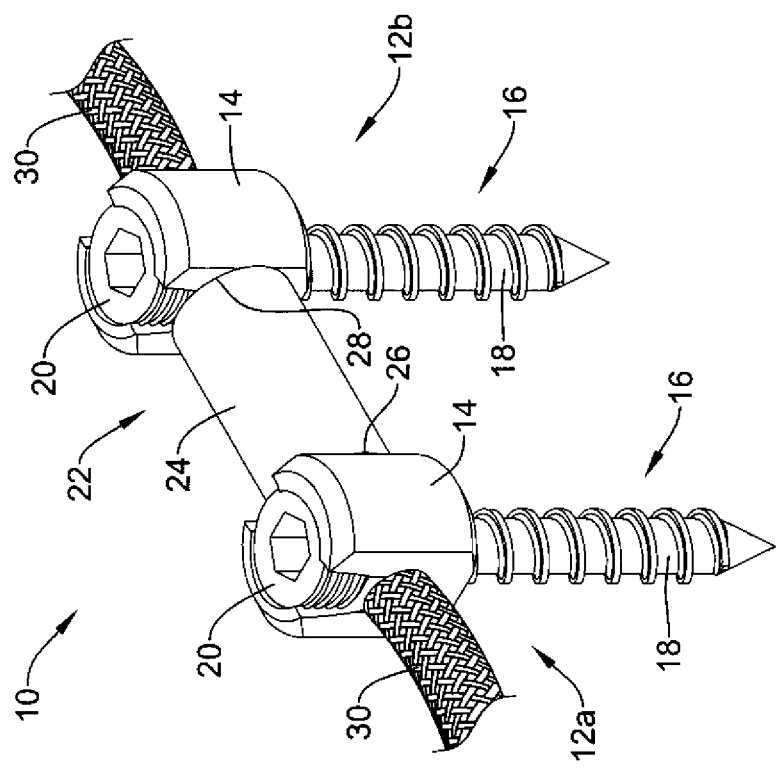
FIG. 1 is a perspective view of an exemplary vertebral stabilization system.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Referring now to FIG. 1, there is shown a vertebral fixation system 10 for stabilizing a portion of a spinal column, such as one or more spinal segments of a spinal column. As used herein, a spinal segment is intended to refer to two or more vertebrae, the intervertebral disc(s) between the vertebrae and other anatomical elements between the vertebrae. For example, a spinal segment may include first and second adjacent vertebrae and the intervertebral disc located between the first and second vertebrae. the spinal stabilization system 10 may provide dynamic stabilization to a spinal segment, preserving and/or allowing for a range of motion of the spinal segment.

In some embodiments, the vertebral stabilization system 10 may be used to treat discogenic low back pain, degenerative spinal stenosis, disc herniations, facet syndrome, posterior element instability, adjacent level syndrome associated with spinal fusion, and/or other maladies associated with the spinal column.

The vertebral stabilization system 10 may include one or more or a plurality of vertebral anchors or fasteners 12. Although the vertebral anchors 12 are depicted as threaded vertebral fasteners (e.g., pedicle screws, bone screws), in some embodiments the vertebral anchors 12 may be vertebral hooks (e.g., laminar hooks) or other types of fastening members for attachment to a bony structure such as a vertebra of the spinal column. Each of the vertebral anchors 12 may be configured to be secured to a vertebra of a spinal column. For instance, the first vertebral anchor 12a may be secured to a first vertebra and the second vertebral anchor 12b may be secured to a second vertebra. Additional vertebral anchors 12 may be present in instances in which the vertebral stabilization system 10 spans three or more vertebra of the spinal column.

The vertebral anchor 12 may include a head portion 14 and a bone engagement portion 16 extending from the head portion 14. In some embodiments, the bone engagement portion 16 may be a shaft portion 18 of the vertebral anchor 12 extending from the head portion 14 along a longitudinal axis of the vertebral anchor 12. In some embodiments, the vertebral anchor 12 may be a monoaxial screw, and in other embodiments the vertebral anchor 12 may be a polyaxial screw. In some embodiments, the shaft portion 18 may be configured to be installed into a bony region of a vertebra of the spinal column. For example, the shaft portion 18 may be installed into a pedicle of a vertebra, or other region of a vertebra. In some embodiments, the shaft portion 18 may be a threaded region having helical threads configured to be screwed into a pedicle of a vertebra, or other bony region of a vertebra.

The vertebral anchor 12 may include a securing element, such as a threaded fastener 20 (e.g., a set screw, cap) configured to engage the head portion 14 to secure a portion of a connecting member 22 to the vertebral anchor 12. For example, the threaded fastener 20 may include threads which mate with threads formed in the head portion 14.

The vertebral stabilization system 10 may also include one or more, or a plurality of connecting members 22 extending between vertebral anchors 12 of the vertebral stabilization system 10. As an illustrative example, the vertebral stabilization system 10 shown in FIG. 1 includes a connecting member 22 extending between the first vertebral anchor 12a and the second vertebral anchor 12b.

The connecting member 22 may be constructed of a plurality of components in some instances. For instance, the connector 22 may include a spacer 24, and a cord 30 extending through the spacer 24, as well as other components if desired.

In some embodiments, the spacer 24 may be an annular spacer having a lumen (not shown) extending from a first end 26 to a second end 28 of the spacer 24. For example, in some embodiments the spacer 24 may be a cylindrical member having a lumen extending therethrough. In other embodiments, the spacer 24 may be molded, extruded, or otherwise formed over and/or around the cord 30. The spacer 24 may be positioned between the head portion 14 of the first vertebral anchor 12a and the head portion 14 of the second vertebral anchor 12b. For instance, when installed between the first and second vertebral anchors 12a, 12b, the first end 26 of the spacer 24 may face, abut or otherwise contact a side surface of the head portion 14 of the first vertebral anchor 12a, and the second end 28 of the spacer 24 may face, abut or otherwise contact a side surface of the head portion 14 of the second vertebral anchor 12b.

The cord 30 may extend from the head portion 14 of the first vertebral anchor 12a to the head portion 14 of the second vertebral anchor 12b. In some embodiments, the cord 30 may extend into and/or extend through a channel, such as a U-shaped channel, extending through the head portion 14 of the first vertebral anchor 12a, and the cord 30 may extend into and/or extend through a channel, such as a U-shaped channel, extending through the head portion 14 of the second vertebral anchor 12b. In some embodiments, the threaded fastener 20 of the first vertebral anchor 12a may be tightened directly onto the cord 30 to retain the cord 30 in the channel of the head portion 14 of the first vertebral anchor 12a, and/or the threaded fastener 20 of the second vertebral anchor 12b may be tightened directly onto the cord 30 to retain the cord in the channel of the head portion 14 of the second vertebral anchor 12b. In other embodiments, the cord 30 may extend into, extend through, and/or be secured to another component which spaces the cord 30 from direct contact with the channel of the vertebral anchor 12a, 12b. For example, the cord 30 may extend into, extend through, and/or be secured to a spindle, spool, sleeve, coupler, or other component, which in turn is secured in the channel of the head portion of the vertebral anchor 12a, 12b with the threaded fastener 20 or other securing fastener. It is noted that during a medical procedure the portions of the cord 30 which are shown extending from the channels of the vertebral anchors 12a, 12b may be trimmed as desired to reduce and/or eliminate the portion of the cord 30 extending from the vertebral anchors 12a, 12b.

When implanted in a patient, the cord 30 of the vertebral stabilization system 10 may limit the range of flexion of the spinal segment, whereas the spacer 24 may limit the range of extension of the spinal segment. In lateral bending and axial rotation, the cord 30 and/or the spacer 24 may limit the range of motion by interacting with each other in a combination of compression, shear and tensile loading. For instance, the cord 30 may be placed in tension and the spacer 24 may be placed in compression between the vertebral anchors 12a, 12b.

The cord 30 may be formed, at least in part, of an elastomeric material, providing the cord 30 with the ability to be elastically elongated under tension, forming an elongateable member of the connector 22. For instance, in some embodiments, one or more filaments or strands of the cord 30 may be formed of an elastomeric material giving the cord 30 a degree of elasticity. In some instances, one or more elastomeric filaments or strands may be intermingled (e.g., woven, braided, knitted) with one or more inelastic, or relatively more inelastic filaments or strands. Some exemplary configurations of the cord 30 are further discussed herein.

The cord 30 may be configured to have a variable stiffness through a range of displacement. For example, the stiffness of the cord may increase as an applied tensile force on the cord 30 is increased. As used herein, the term stiffness of the cord is intended to refer to the tensile force (i.e., load) divided by the displacement of the cord subjected to the applied tensile force. Thus, stiffness (e.g., N/mm) equals force (e.g., Newtons) divided by displacement (e.g., millimeters).

Figure 2:
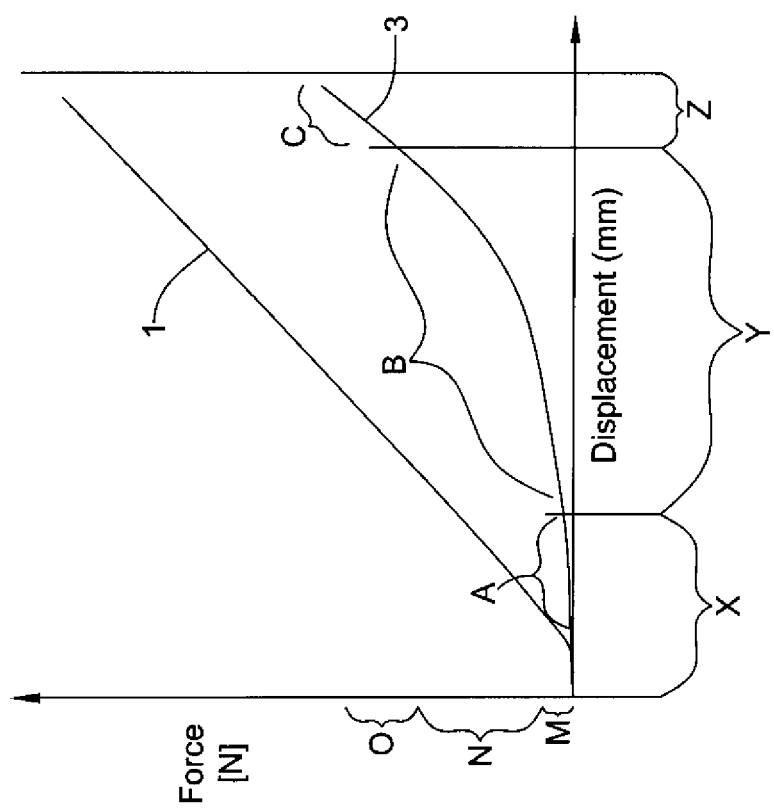
FIG. 2 is a graph illustrating characteristics of the cord of the vertebral stabilization system of FIG. 1.

FIG. 2 is a graph of a representative curve illustrating the variable stiffness of the cord 30. The Y-axis of the graph indicates the tensile force (e.g., load) applied to the cord 30 while the X-axis of the graph indicates the displacement (e.g., elongation, strain) of the cord 30 for a given amount of tensile loading of the cord 30. Line 3 is a representation of the change in stiffness of the cord 30 throughout a range of displacement of the cord 30. Thus, the slope of the line 3 indicates the stiffness of the cord 30. As can be seen from line 3, the stiffness of the cord 30 may increase as an applied tensile force on the cord 30 is increased. Also shown in FIG. 2 is a line 1 representing a cord of the prior art having a singular stiffness throughout displacement of the cord from tensile loading. As can be seen from line 1, the stiffness of a cord of the prior art does not increase as an applied tensile force on the cord is increased. The behavior of the cord 30, in which the stiffness of the cord 30 increases with increasing tensile load, may more closely approximate the behavior of a native spinal column, as well as have other advantageous characteristics.

As can be seen from line 3 of FIG. 2, the cord 30 may include a plurality of phases or regions of stiffness, for example, three phases of stiffness throughout displacement of the cord 30 from tensile loading. A configuration of the cord 30 having three phases of stiffness may be referred to as a triphasic cord. In other embodiments the cord 30 may have another number of phases of stiffness, such as two, four, five, six or more phases.

The cord 30 may include a first phase of stiffness A through a first range of displacement (e.g., elongation, strain) and/or tensile loading, a second phase of stiffness B through a second range of displacement and/or tensile loading, and a third phase of stiffness C through a third range of displacement and/or tensile loading. In some embodiments, the cord 30 may include one or more additional phases of stiffness through one or more additional ranges of displacement and/or tensile loading, if desired.

In some embodiments, the stiffness of the cord 30 in the first phase of stiffness A may be 50% or less, 40% or less, 30% or less, 25% or less, 20% or less, 10% or less, or 5% or less of the stiffness of the cord 30 in the third phase of stiffness C.

The first phase of stiffness A may be called the dynamic phase of the cord 30. It can be appreciated that through this first phase of stiffness A, the cord 30 may have a first stiffness (e.g., a very low stiffness) through an initial range of displacement from a neutral or starting position of the cord 30. By providing the cord 30 with a very low stiffness through an initial range of displacement, the cord 30 may provide the vertebral segment to which the vertebral stabilization system 10 is implanted a high degree of mobility around the neutral or starting position of the cord 30. Therefore, when the vertebral segment, and thus the cord 30, is subjected to low loading, the vertebral stabilization system 10 maintains a large degree of mobility for the vertebral segment allowing for a greater range of motion of the vertebral segment.

The second phase of stiffness B may be called the transition or progressively stabilizing phase of the cord 30. It can be appreciated that through this phase of stiffness B, the stiffness of the cord 30 may progressively increase from the stiffness of the cord 30 in the first phase to the stiffness of the cord 30 in the third phase.

The third phase of stiffness C may be called the limiting phase of the cord 30. It can be appreciated that through this phase of stiffness C, the stiffness of the cord 30 is greater than the stiffness of the cord 30 through the first phase of stiffness A. The third phase of stiffness C may provide a limiting effect to the cord 30, limiting further displacement of the cord 30 at high levels of loading. By providing the cord 30 with a greater stiffness through this stage, the cord 30 may provide the vertebral segment to which the vertebral stabilization system 10 is implanted a high degree of stability and/or rigidity when subjected to high levels of loading, providing an end stop to the amount of flexion allowed by the vertebral stabilization system 10.

In some embodiments, the first phase of stiffness A may be less than about 200 Newtons per millimeter (N/mm), less than about 150 N/mm, less than about 100 N/mm, or less than about 75 N/mm, and the third phase of stiffness C may be greater than about 150 N/mm, greater than about 200 N/mm, greater than about 225 N/mm, greater than about 250 N/mm, greater than about 275 N/mm, or greater than about 300 N/mm. The second phase of stiffness B may be a phase of transition from the first phase of stiffness A to the third phase of stiffness C. For instance, in some embodiments the second phase of stiffness B may be a phase in which the stiffness of the cord 30 progressively increases from the first phase of stiffness A to the third phase of stiffness C.

In some embodiments, the first phase of stiffness A may be in the range of about 0 N/mm to about 100 N/mm, the second phase of stiffness B may be in the range of about 100 N/mm to about 200 N/mm, and the third phase of stiffness C may be greater than about 200 N/mm. In other embodiments, the first phase of stiffness A may be in the range of about 0 N/mm to about 100 N/mm, the second phase of stiffness B may be in the range of about 100 N/mm to about 250 N/mm, and the third phase of stiffness C may be greater than about 250 N/mm.

The cord 30 may exhibit the first phase of stiffness A through a first range of displacement X and through a first range of tensile loading M. The cord 30 may exhibit the second phase of stiffness B through a second range of displacement Y, and through a second range of tensile loading N. The cord 30 may exhibit the third phase of stiffness C through a third range of displacement Z and through a third range of tensile loading O. The second range of displacement Y may be greater than the first range of displacement X, and the third range of displacement Z may be greater than the second range of displacement Y. The second range of tensile loading N may be greater than the first range of tensile loading M, and the third range of tensile loading O may be greater than the second range of tensile loading N.

For instance, the first range of displacement X of the cord 30, in which the cord 30 may exhibit the first phase of stiffness A, may be in the range of about 3 millimeters or less, about 2.5 millimeters or less, about 2 millimeters or less, about 1.5 millimeters or less, or about 1 millimeter or less from the neutral or starting position of the cord 30 when implanted with the vertebral stabilization system 10 in a patient.

The third range of displacement Z of the cord 30, in which the cord 30 may exhibit the third phase of stiffness C, may be in the range of about 3 millimeters or more, about 3.5 millimeters or more, about 4 millimeters or more, about 4.5 millimeters or more, or about 5 millimeters or more from the neutral or starting position of the cord 30 when implanted with the vertebral stabilization system 10 in a patient.

The second range of displacement Y of the cord 30, in which the cord 30 may exhibit the second phase of stiffness B, may be a range of displacement of the cord 30 between the upper extent of the first range of displacement X of the cord 30 and the lower extent of the third range of displacement Z of the cord 30. The lower extent of the third range of displacement Z of the cord 30 may be greater than the upper extent of the first range of displacement X of the cord 30. In some embodiments, second range of displacement Y of the cord 30 may be from about 1, 1.5, 2, 2.5 or 3 millimeters to about 3, 3.5, 4, 4.5 or 5 millimeters in some instances.

The first range of tensile loading M of the cord 30, in which the cord 30 may exhibit the first phase of stiffness A, may be in the range of 0 Newtons (N) to about 100 N, about 150 N, about 200 N or about 250 N. Thus, the first range of tensile loading M may be less than about 250 N, less than about 200 N, less than about 150 N, or less than about 100 N in some embodiments.

The third range of tensile loading O of the cord 30, in which the cord 30 may exhibit the third phase of stiffness C, may be about 300 N and greater, about 350 N and greater, about 400 N and greater, about 450 N and greater, or about 500 N and greater in some embodiments.

The second range of tensile loading N of the cord 30, in which the cord 30 may exhibit the second phase of stiffness B, may be a range of tensile loading of the cord 30 between the upper extent of the first range of tensile loading M of the cord 30, and the lower extent of the third range of tensile loading O of the cord 30. The lower extent of the third range of tensile loading O of the cord 30 may be greater than the upper extent of the first range of tensile loading M of the cord 30. In some embodiments, the second range of tensile loading N of the cord 30 may be from about 100 N to about 500 N, about 150 N to about 450 N, or about 200 N to about 400 N.

Thus, from FIG. 2 it can be seen that the cord 30 may have a variable stiffness throughout the first, second and third ranges of tensile loading M, N, O, respectively, in which the second range of tensile loading N is greater than the first range of tensile loading M, and the third range of tensile loading O is greater than the second range of tensile loading N. In such an embodiment, the stiffness of the cord 30 through the first range of tensile loading M is less than the stiffness of the cord 30 through the second range of tensile loading N, and the stiffness of the cord 30 through the third range of tensile loading O is greater than the stiffness of the cord 30 through the second range of tensile loading N. In some embodiments, the stiffness of the cord 30 through the first range of tensile loading M is less than the stiffness of the cord 30 through the third range of tensile loading O, and the stiffness of the cord 30 through the second range of tensile loading N progressively increases from that of the first range of tensile loading M to that of the third range of tensile loading O.

Figure 3:
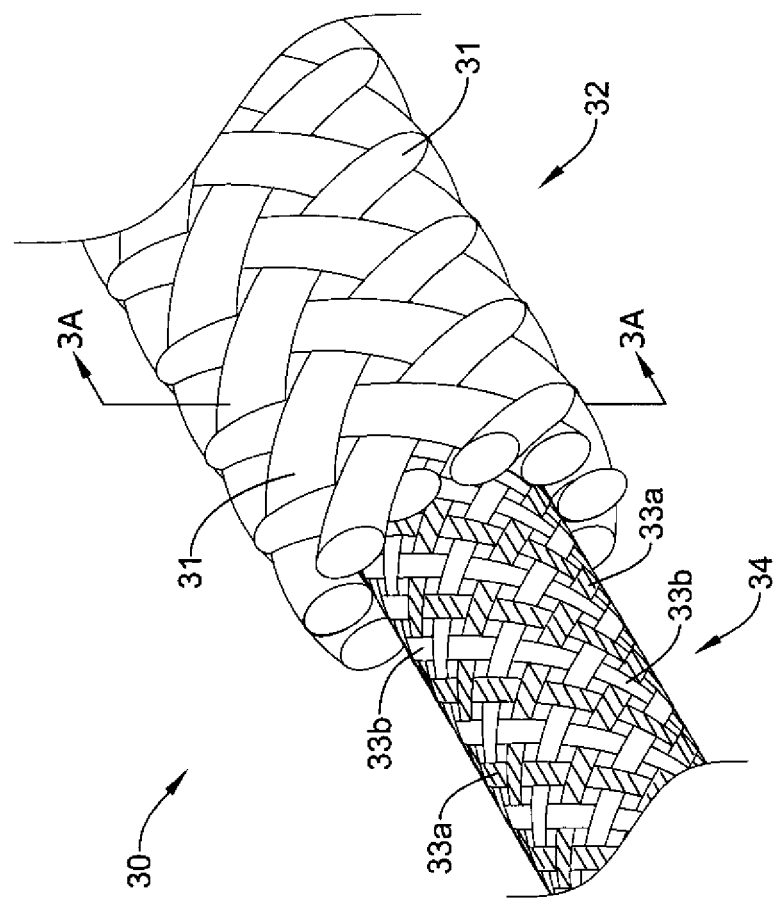
FIG. 3 is a perspective view of one embodiment of the cord of the vertebral stabilization system.

One exemplary embodiment of the cord 30 is illustrated in FIG. 3. The cord 30 may include a plurality of filaments 31 forming an outer layer 32 of the cord 30, and the cord 30 may include a plurality of filaments 33 forming an inner layer 34 of the cord 30. The inner layer 34 of the cord 30 is located within the outer layer 32 of the cord 30, and in some embodiments may be an innermost layer of the cord 30. In other embodiments, the cord 30 may include one or more additional layers located within the inner layer 34. For example, the cord 30 may include a central layer or core layer located within the inner layer 34. The outer layer 32 of the cord 30 is located exterior of the inner layer 34, and in some embodiments may be an outermost layer of the cord 30. In other embodiments, the cord 30 may include one or more additional layers located exterior of the outer layer 32, such as a braid layer, a coating, a jacket, a sleeve, or other layer of material.

The plurality of filaments 33 forming the inner layer 34 may be braided, woven, knitted, twisted or otherwise intermingled to form the inner layer 34 in some embodiments. Thus, in some embodiments the inner layer 34 may be a braided, woven, knitted, or twisted layer of the cord 30. The inner layer 34 may include any desired number of filaments 33. For example, the inner layer 34 may include 1, 2, 4, 8, 16, 20, 24, 28, or 32 filaments 33 in some instances.

As shown in FIG. 3, the inner layer 34 may include a first subset of filaments 33a having a first elasticity and a second subset of filaments 33b having a second elasticity different from the first elasticity of the first subset of filaments 33a. It is noted, however, that in other embodiments the inner layer 34 may be formed of a plurality of filaments formed of a material, each of which has the same or similar elasticity.

For instance, the first subset of filaments 33a may be considered a more compliant, elastic component of the inner layer 34 of the cord 30. The first subset of filaments 33a, which may be referred to as elastic filaments, may be formed of a material exhibiting high elastic recovery and low plastic deformation. For instance, the material of the elastic filaments 33a, which may be a polymer in some cases, may have a tensile strength of more than 100 MPa, preferably more than 500 MPa, and a tensile modulus of elasticity (Young's Modulus) of less than 1 GPa. Some suitable materials for the elastic filaments 33a include, but are not limited to, thermoplastic polyurethanes (e.g., polycarbonate urethane, polyetherurethane), polyetheresters, polyetherethers, polyolefinic elastomers, EPM (ethylene propylene rubber), EPDM rubber (ethylene propylene diene rubber), epichlorohydrin rubber, polyacrylic rubber, silicone rubber, fluorosilicone rubber, fluoroelastomers, perfluoroelastomers, polyether block amides, chlorosulfonated polyethylene, ethylene-vinyl acetate, thermoplastic elastomers, thermoplastic vulcanizates, thermoplastic olefins (e.g., syndiotactic polypropylene), polysulfide rubber and copolymers, blends or combinations thereof.

In some embodiments in which the inner layer 34 is formed solely of filaments of one desired material, the filaments of the inner layer 34 may be elastic filaments formed of an elastic material such as one of the materials listed above or other desired material.

The second subset of filaments 33b may be considered a stiff, load bearing component of the inner layer 34 of the cord 30. The second subset of filaments 33b, which may be referred to as stiff reinforcement filaments, may be formed of a material exhibiting strong, stiff characteristics having low elastic elongation. For instance, the material of the stiff reinforcement filaments 33b, which may be a polymer in some cases, may have a tensile strength of more than 100 MPa, preferably more than 500 MPa, and a tensile modulus of elasticity (Young's Modulus) of more than 1 GPa, preferably more than 3 GPa. Some suitable materials for the stiff reinforcement filaments 33b include, but are not limited to, polyethylene terephthalate, polybutylene terephthalate, polyethylene naphthalate, polyethylene, polypropylene, polyethylene oxide, polyethylene glycol, polypropylene oxide, polyoxymethylene, polytetrafluoroethylene, polyurethane, polyetherurethane, polycarbonate urethane, polyamide, polyimide, polyetherimide, polyetheretherketone, polyaryletherketone, polyvinylchloride, polystyrene, polycarbonate, polyphenylsulfone, polysulfone, acrylics, silicones and copolymers, blends or combinations thereof.

In some embodiments in which the inner layer 34 is formed solely of filaments of one desired material, the filaments of the inner layer 34 may be stiff filaments formed of a stiff material such as one of the materials listed above, or other desired material.

The elastic filaments 33a and the stiff filaments 33b may be included in the inner layer 34 in any desired proportions as needed to attain the desired mechanical requirements of the cord 30. For instance, there may be an equivalent number of elastic filaments 33a to the number of stiff filaments 33b in the inner layer 34 in some embodiments. In other embodiments, the elastic filaments 33a may make up a majority of the filaments of the inner layer 34 and the stiff filaments 33b may make up a minority of the filaments of the inner layer 34. In yet other embodiments, the elastic filaments 33a may make up a minority of the filaments of the inner layer 34 and the stiff filaments 33b may make up a majority of the filaments of the inner layer 34.

The plurality of filaments 31 forming the outer layer 32 may be braided, woven, knitted, twisted or otherwise intermingled to form the outer layer 32 in some embodiments. Thus, in some embodiments the outer layer 32 may be a braided, woven, knitted, or twisted layer of the cord 30. The outer layer 32 may include any desired number of filaments 31. For example, the outer layer 32 may include 1, 2, 4, 8, 16, 20, 24, 28, or 32 filaments 31 in some instances.

The filaments 31 may be formed of any of the materials listed above, including those included with the stiff filaments 33b, or other desired materials. In some embodiments, each of the filaments of the outer layer 32 may be formed of a single material, while in other embodiments the outer layer 32 may be formed of multiple filaments of two or more different materials. For example, in some embodiments, the outer layer 32, which may be a braided outermost layer of the cord 30, may be formed solely of polyethylene terephthalate (PET) filaments. It is thought that an outermost layer including only braided polyethylene terephthalate (PET) filaments may be beneficial for abrasion resistance.

Figure 3A:
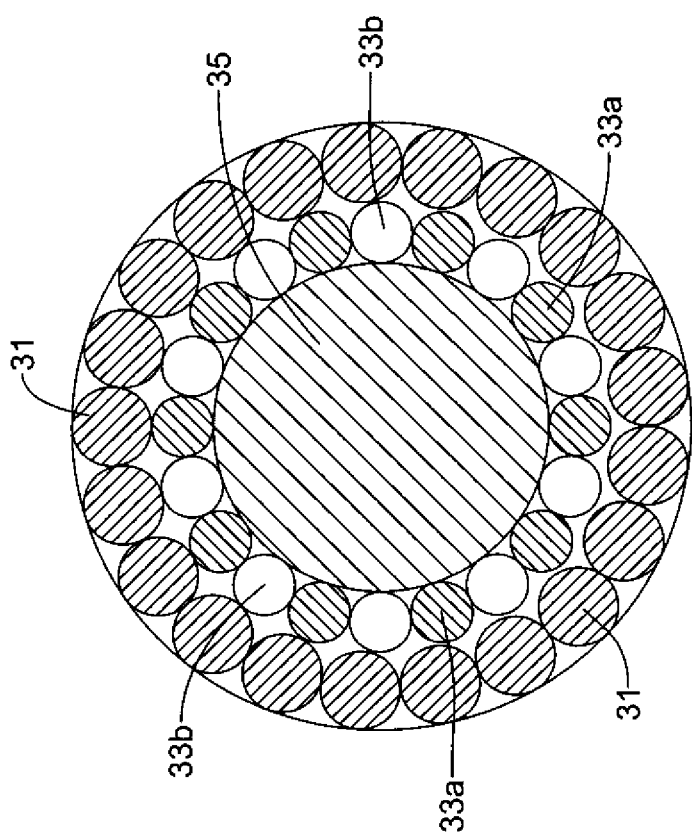
FIG. 3A is a transverse cross-sectional view of the cord of FIG. 3 taken along line 3A-3A.

As shown in FIG. 3A, in some embodiments, the cord 30 may include a core 35 extending through the inner layer 34. In some embodiments, the core 35 may include a piece of material, such as one or more strands or filaments of material, extending axially through the cord 30. In other embodiments, the core 35 may include a plurality of strands or filaments of material extending along the central axis of the cord 30 in a twisted, braided, woven, or otherwise intermingled fashion. The core 35 may be formed of any of the materials listed above, or other desired materials.

Polymers intended for use for one or more of the filaments 31, 33a and 33b and/or core 35 may be unfilled or filled with carbon, glassy, metallic, ceramic or polymeric inclusions with macro-, micro-, or nanoscale dimensions and may be discontinuous or continuous fiber, ribbon, needle, ellipsoid, cylindrical, platelet, disk, spherical, cubic, regular or irregular geometries, or a combination thereof, in a range of volume fractions and size distributions. These particles may be biostable or biodegradable in situ. The incorporation of these particles may contribute to mechanical performance, biological performance, remote detection (e.g., radiopacity), degradation resistance or acceleration, delivery of a drug, therapeutic agent, or other active ingredient, or a combination thereof.

Through an initial range of axial loading, the axial load may be transferred, at least primarily, through the inner layer 34, and through further ranges of axial loading the axial load may be reallocated between both the inner layer 34 and the outer layer 32. Thus, as the axial load is transferred to the outer layer 32, the stiffness of the cord 30 may increase. Thus, the inner layer 34 may dictate the stiffness of the cord 30 through a first range of displacement and/or axial loading of the cord 30, and the outer layer 32 may dictate the stiffness of the cord 30 through a second range of displacement and/or axial loading of the cord 30, greater than the first range of displacement and/or axial loading.

Figure 4A:
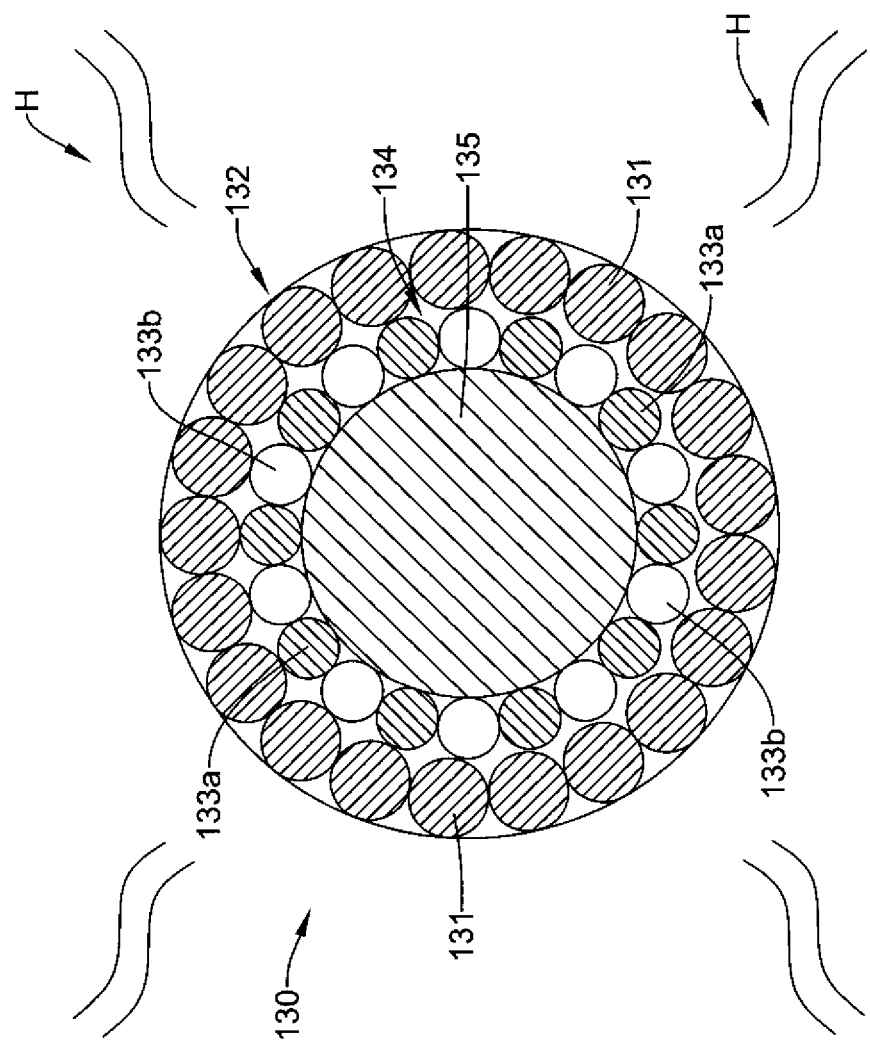
FIGS. 4A and 4B illustrate an alternative configuration of a cord for use in a vertebral stabilization system and method for constructing the cord.
Figure 4B:
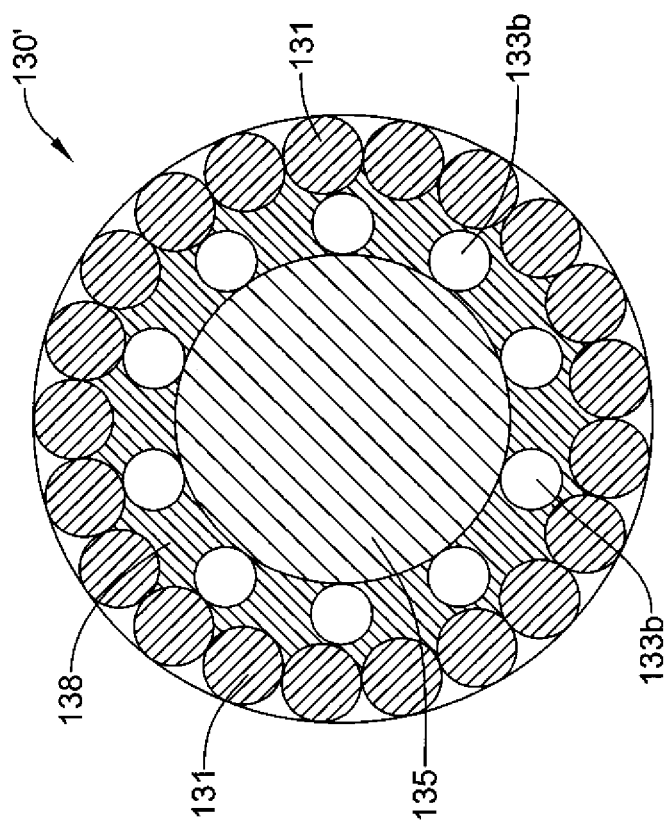

FIGS. 4A and 4B illustrate an alternative configuration of a cord 130 and method for constructing the cord 130. The cord 130 may include an outer layer 132 formed of a plurality of filaments 131 surrounding an inner layer 134 formed of a plurality of filaments 133 similar to that of the cord 30. The cord 130 may optionally also include a central core material 135 located within the inner layer 134. The core 135 may be similar in material, construction, and/or configuration to the core 35 discussed above.

The plurality of filaments 131 forming the outer layer 132 may be braided, woven, knitted, twisted or otherwise intermingled to form the outer layer 132 in some embodiments. Thus, in some embodiments the outer layer 132 may be a braided, woven, knitted, or twisted layer of the cord 130. Furthermore, the plurality of filaments 133 forming the inner layer 134 may be braided, woven, knitted, twisted or otherwise intermingled to form the inner layer 134 in some embodiments. Thus, in some embodiments the inner layer 134 may be a braided, woven, knitted, or twisted layer of the cord 130.

The inner layer 134 may include a first subset of filaments 133a dissimilar to a second subset of filaments 133b. For instance, the first subset of filaments 133a may be formed of a material having a melting temperature, and the second subset of filaments 133b may be formed of a material having a critical temperature, such as a melting temperature, glass transition temperature or a relaxation temperature, different from the melting temperature of the first material. The melting temperature of the first subset of filaments 133a may be less than the critical temperature of the second subset of filaments 133b. The material of the first subset of filaments 133a may be one of the materials listed above regarding possible materials of the filaments 33a, or another material if desired. The material of the second subset of filaments 133b may be one of the materials listed above regarding possible materials of the filaments 33b, or another material if desired.

The cord structure 130 shown in FIG. 4A may be heated with a heat source H to a temperature greater than the melting temperature of the first subset of filaments 133a, but less than the critical temperature of the second subset of filaments 133b. Upon heating the cord structure 130, the elastic material of the first subset of filaments 133a will flow around adjacent filaments 133b, and in some instances bond onto adjacent filaments 133b of the inner layer 134. The presence of the outer layer 132 may constrain the molten material within the confines of the outer layer 132, or another layer or sleeve may be placed over the cord 130 to constrain the molten material. The cord structure 130 may then be allowed to cool to a temperature below the melting temperature of the material of the first subset of filaments 133a, at which point the material of the first subset of filaments 133a would solidify. The modified cord 130' results in a solid elastic body 138 of the elastic material of the first subset of filaments 133a surrounding or encasing the filaments of the second subset of filaments 133b. Thus, the second subset of filaments 133b may be embedded (e.g., partially or fully embedded) in an elastic matrix of the elastic material of the solid elastic body 138. The solid elastic body 138 may provide the cord 130' with a degree of elasticity, while the filaments 133b embedded in the solid elastic body 138 and/or the filaments 131 of the outer layer 132 may provide the cord 130' with a degree of rigidity or stiffness. Furthermore, the solid elastic body 138 may restrict decreases in braid angle during axial loading of the cord 130', providing a degree of rigidity or stiffness to the cord 130'.

In one specific example, the first subset of filaments 133a, may be formed of an elastic material and the second subset of filaments 133b may be formed of polyethylene terephthalate (PET). The elastic material of the first subset of filaments 133a may have a melting temperature less than the relaxation temperature of the PET material of the second subset of filaments 133b. The cord structure 130 shown in FIG. 4A may be heated with a heat source H to a temperature greater than the melting temperature of the first subset of filaments 133a, but less than the relaxation temperature of the second subset of filaments 133b. Upon heating the cord structure 130, the elastic material of the first subset of filaments 133a will flow around adjacent filaments 133b, and in some instances bond onto adjacent filaments 133b of the inner layer 134. The cord structure 130 may then be allowed to cool to a temperature below the melting temperature of the material of the first subset of filaments 133a, at which point the material of the first subset of filaments 133a would solidify. The modified cord 130' results in a solid elastic body 138 of the elastic material of the first subset of filaments 133a surrounding or encasing the PET filaments of the second subset of filaments 133b. Thus, the PET filaments 133b may be embedded in an elastic matrix of the elastic material of the solid elastic body 138.

Through an initial range of axial loading, the axial load may be transferred, at least primarily, through the inner layer 134, and through further ranges of axial loading the axial load may be reallocated between both the inner layer 134 and the outer layer 132. Thus, as the axial load is transferred to the outer layer 132, the stiffness of the cord 130' may increase. Thus, the inner layer 134 may dictate the stiffness of the cord 130' through a first range of displacement and/or axial loading of the cord 130', and the outer layer 132 may dictate the stiffness of the cord 130' through a second range of displacement and/or axial loading of the cord 130', greater than the first range of displacement and/or axial loading.

Figure 5A:
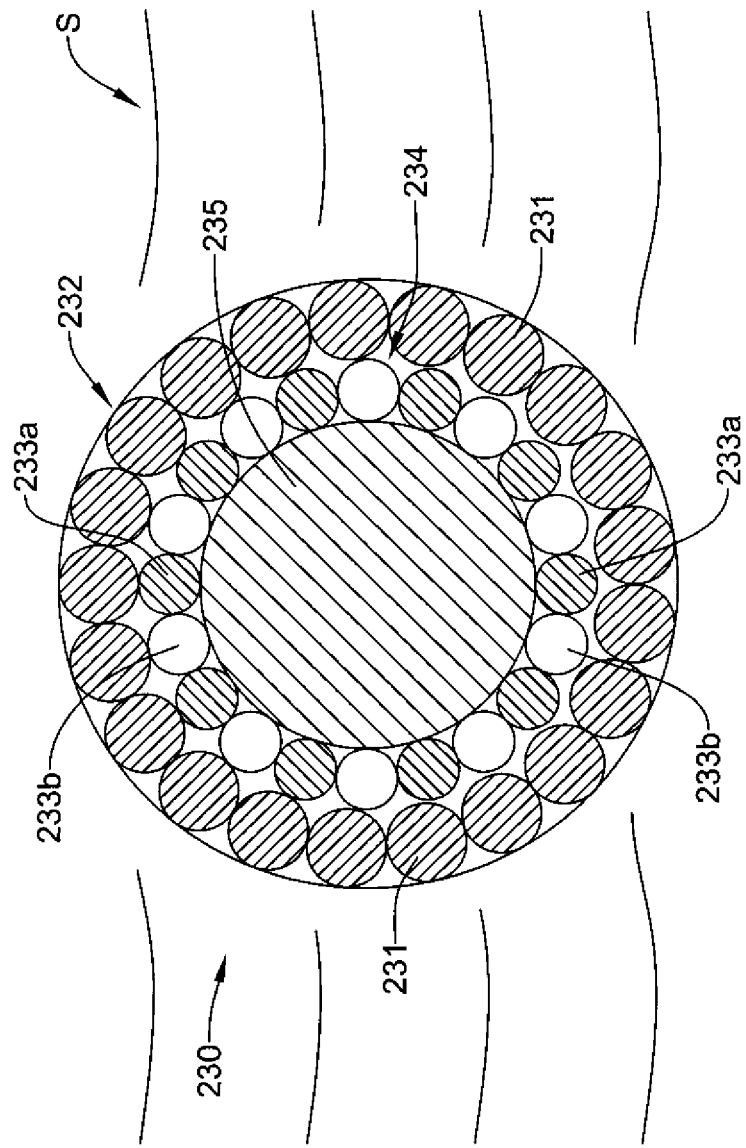
FIGS. 5A and 5B illustrate an alternative configuration of a cord for use in a vertebral stabilization system and method for constructing the cord.
Figure 5B:
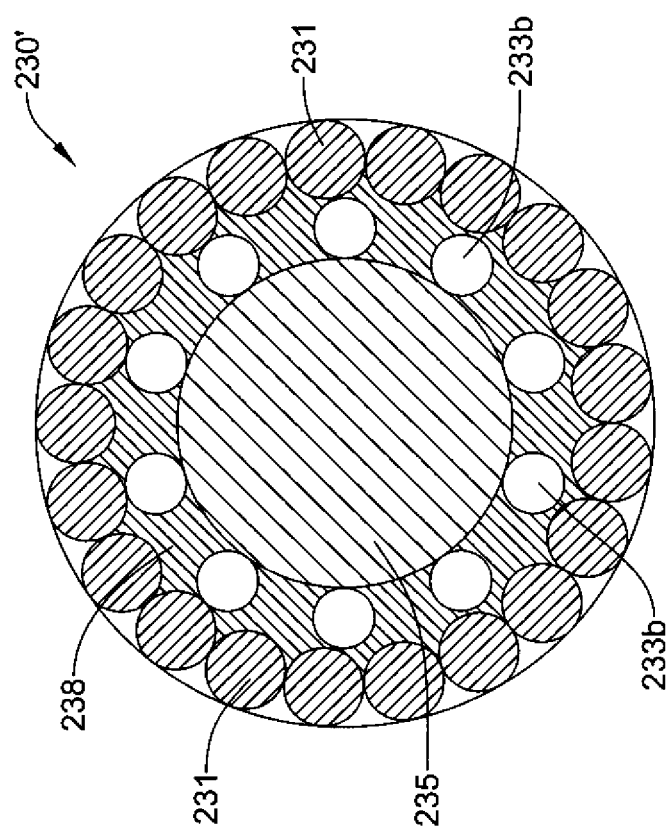

FIGS. 5A and 5B illustrate an alternative configuration of a cord 230 and method for constructing the cord 230. The cord 230 may include an outer layer 232 formed of a plurality of filaments 231 surrounding an inner layer 234 formed of a plurality of filaments 233 similar to that of the cord 30. The cord 230 may optionally also include a central core material 235 located within the inner layer 234. The core 235 may be similar in material, construction, and/or configuration to the core 35 discussed above.

The plurality of filaments 231 forming the outer layer 232 may be braided, woven, knitted, twisted or otherwise intermingled to form the outer layer 232 in some embodiments. Thus, in some embodiments the outer layer 232 may be a braided, woven, knitted, or twisted layer of the cord 230. Furthermore, the plurality of filaments 233 forming the inner layer 234 may be braided, woven, knitted, twisted or otherwise intermingled to form the inner layer 234 in some embodiments. Thus, in some embodiments the inner layer 234 may be a braided, woven, knitted, or twisted layer of the cord 230.

The inner layer 234 may include a first subset of filaments 233a dissimilar to a second subset of filaments 233b. For instance, the first subset of filaments 133a may be formed of a material which is soluble or dissolvable when subjected to a selected solvent, and the second subset of filaments 133b may be formed of a material which is not soluble or dissolvable when subjected to the selected solvent. The material of the first subset of filaments 233a may be one of the materials listed above regarding possible materials of the filaments 33a, or another material if desired. The material of the second subset of filaments 233b may be one of the materials listed above regarding possible materials of the filaments 33b, or another material if desired.

The cord structure 230 shown in FIG. 5A may be subjected to a solvent S, such as immersed or submerged in a solvent S which dissolves the elastic material of the first subset of filaments 233a, but does not dissolve the material of the second subset of filaments 233b, forming a solution of the dissolved elastic material in the solvent. The presence of the outer layer 232 may constrain the solution within the confines of the outer layer 232, or another layer or sleeve may be placed over the cord 230 to constrain the solution. The solution, including the dissolved elastic material may flow between and around the filaments 233b. The solvent may then be removed, for example, by evaporation or otherwise, at which point the elastic material of the first subset of filaments 233a would consolidate and solidify. The modified cord 230' results in a solid elastic body 238 of the elastic material of the first subset of filaments 233a surrounding or encasing the filaments of the second subset of filaments 233b. Thus, the second subset of filaments 233b may be embedded (e.g., partially or fully embedded) in an elastic matrix of the elastic material of the solid elastic body 238. This structure 230' may resemble the cord structure 130' discussed above, without necessitating the cord structure 230' to exposure to elevated temperatures in some embodiments. In some embodiments, however, it may be desired to perform a combination of using solvents and/or elevated temperatures to manipulate the cord construct.

The solid elastic body 238 may provide the cord 230' with a degree of elasticity, while the filaments 233b embedded in the solid elastic body 238 and/or the filaments 231 of the outer layer 232 may provide the cord 230' with a degree of rigidity or stiffness. Furthermore, the solid elastic body 238 may restrict decreases in braid angle during axial loading of the cord 230', providing a degree of rigidity or stiffness to the cord 230'.

In one specific example, the first subset of filaments 233a, may be formed of an elastic material and the second subset of filaments 233b may be formed of polyethylene terephthalate (PET). The elastic material of the first subset of filaments 233a may readily dissolved in a solvent, while the PET material of the second subset of filaments 233b may not be readily dissolved in the solvent. The solvent may then be removed, allowing the elastic material of the first subset of filaments 233a to consolidate and solidify, forming a solid elastic body 238 of the elastic material of the first subset of filaments 233a surrounding or encasing the PET filaments of the second subset of filaments 233b. Thus, the PET filaments 233b may be embedded in an elastic matrix of the elastic material of the solid elastic body 238.

Through an initial range of axial loading, the axial load may be transferred, at least primarily, through the inner layer 234, and through further ranges of axial loading the axial load may be reallocated between both the inner layer 234 and the outer layer 232. Thus, as the axial load is transferred to the outer layer 232, the stiffness of the cord 230' may increase. Thus, the inner layer 234 may dictate the stiffness of the cord 230' through a first range of displacement and/or axial loading of the cord 230', and the outer layer 232 may dictate the stiffness of the cord 230' through a second range of displacement and/or axial loading of the cord 230', greater than the first range of displacement and/or axial loading.

Figure 6A:
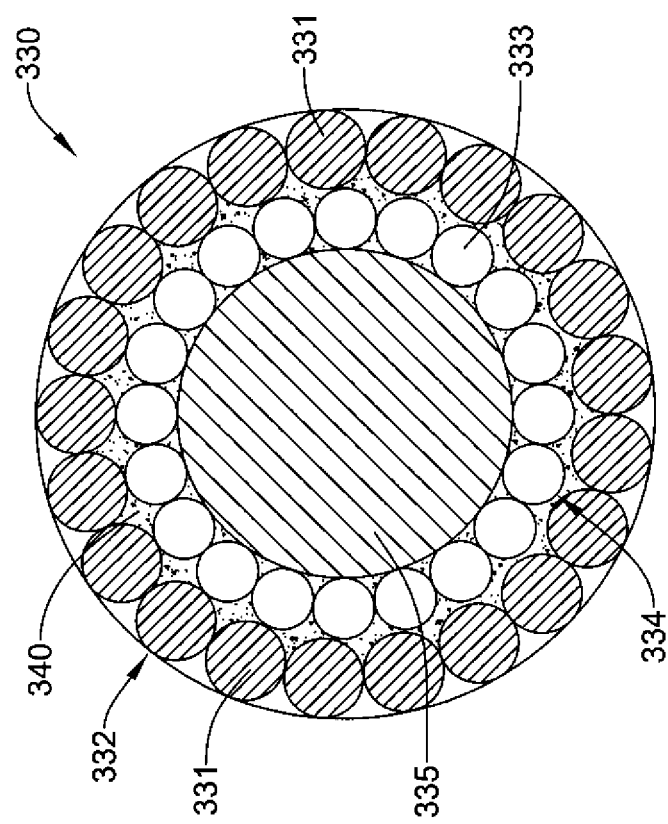
FIGS. 6A and 6B illustrate an alternative configuration of a cord for use in a vertebral stabilization system and method for constructing the cord.
Figure 6B:
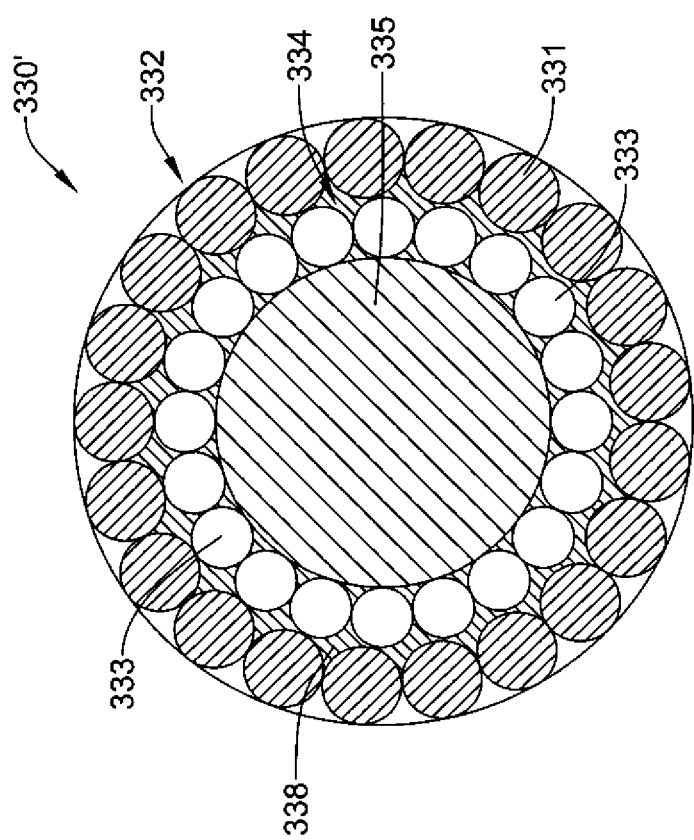

FIGS. 6A and 6B illustrate an alternative configuration of a cord 330 and method for constructing the cord 330. The cord 330 may include an outer layer 332 formed of a plurality of filaments 331 surrounding an inner layer 334 formed of a plurality of filaments 333 similar to that of the cord 30. The cord 330 may optionally also include a central core material 335 located within the inner layer 334. The core 335 may be similar in material, construction, and/or configuration to the core 35 discussed above.

The plurality of filaments 331 forming the outer layer 232 may be braided, woven, knitted, twisted or otherwise intermingled to form the outer layer 332 in some embodiments. Thus, in some embodiments the outer layer 332 may be a braided, woven, knitted, or twisted layer of the cord 330. Furthermore, the plurality of filaments 333 forming the inner layer 334 may be braided, woven, knitted, twisted or otherwise intermingled to form the inner layer 334 in some embodiments. Thus, in some embodiments the inner layer 334 may be a braided, woven, knitted, or twisted layer of the cord 330. The material of the filaments 331, 333 of the outer layer 332 and/or the inner layer 334 may be one of the materials listed above regarding possible materials of the filaments 33a, 33b, or another material if desired.

A filler 340 of an elastic material may fill the space between the filaments 333 of the inner layer 334 and the filaments 331 of the outer layer 332. For instance, in some embodiments the filler 340 may be a powder of an elastic material in dry form. In other embodiments the filler 340 may include an elastic material suspended in a liquid. In other embodiments the filler 340 may include an elastic material in a film form. The elastic material of the filler 340 may be one of the materials listed above regarding possible materials of the filaments 33a, or another material if desired.

The elastic material of the filler 340 may subsequently be caused to flow by melting and/or dissolving the elastic material. In some embodiments, it may be desired to perform a combination of using solvents and/or elevated temperatures to manipulate the cord construct. For example, the cord 330 may be subjected to an elevated temperature and/or submerged in a solvent to melt and/or dissolve the elastic material of the filler 340. The elastic material may then flow around the filaments 333 of the inner layer 334 and/or the confines of the outer layer 332. The presence of the outer layer 332 may constrain the elastic material within the confines of the outer layer 332, or another layer or sleeve may be placed over the cord 330 to constrain the elastic material. Subsequently, cooling the elastic material and/or removing the solvent may consolidate and solidify the elastic material into a solid elastic body 338.

The modified cord 330', shown in FIG. 6B results in the solid elastic body 338 of the elastic material of the filler 340 surrounding or encasing the filaments 333 of the inner layer 334. Thus, the filaments 333 of the inner layer 334 may be embedded (e.g., partially or fully embedded) in an elastic matrix of the elastic material of the solid elastic body 338.

The solid elastic body 338 may provide the cord 330' with a degree of elasticity, while the filaments 333 embedded in the solid elastic body 338 and/or the filaments 331 of the outer layer 332 may provide the cord 330' with a degree of rigidity or stiffness. Furthermore, the solid elastic body 338 may restrict decreases in braid angle during axial loading of the cord 330', providing a degree of rigidity or stiffness to the cord 330'.

In one specific example, the filaments 333 of the inner layer 334 may be formed of polyethylene terephthalate (PET). Thus, the PET filaments 333 may be embedded in an elastic matrix of the elastic material of the solid elastic body 338.

In some embodiments, the filaments 333 of the inner layer 334, such as filaments formed of PET, may be impregnated with a solution of the elastic material by dipping, spraying, etc. and subsequently removing the solvent. In other embodiments, the filaments 333 of the inner layer 334, such as filaments formed of PET, may be impregnated with a melt of the elastic material by dipping, spraying, etc. and subsequently cooling the elastic material.

Through an initial range of axial loading, the axial load may be transferred, at least primarily, through the inner layer 334, and through further ranges of axial loading the axial load may be reallocated between both the inner layer 334 and the outer layer 332. Thus, as the axial load is transferred to the outer layer 332, the stiffness of the cord 330' may increase. Thus, the inner layer 334 may dictate the stiffness of the cord 330' through a first range of displacement and/or axial loading of the cord 330', and the outer layer 332 may dictate the stiffness of the cord 330' through a second range of displacement and/or axial loading of the cord 330', greater than the first range of displacement and/or axial loading.

Figure 7A:
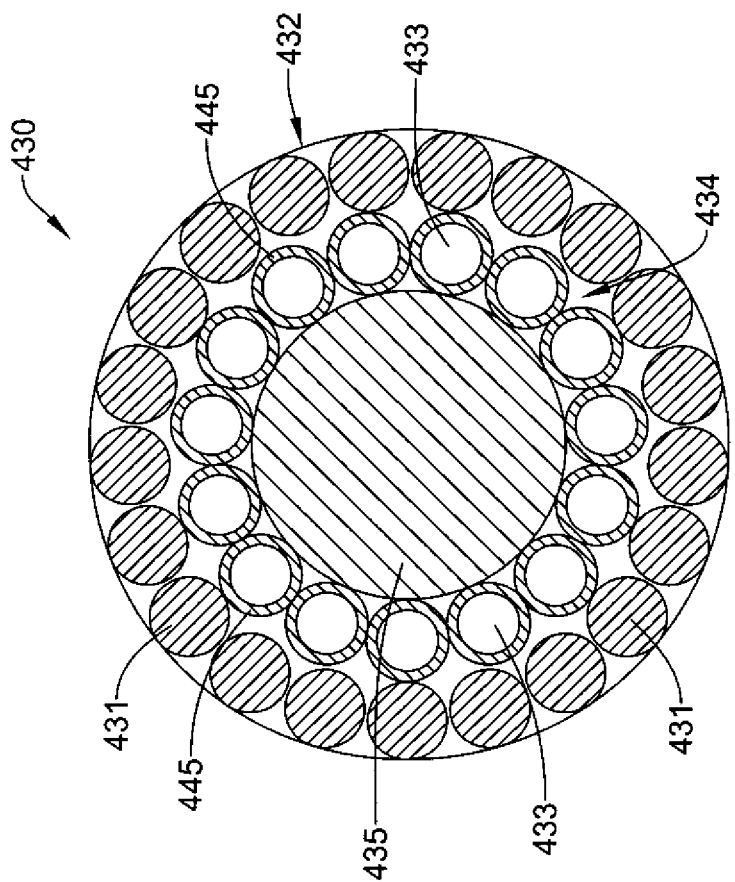
FIGS. 7A and 7B illustrate an alternative configuration of a cord for use in a vertebral stabilization system and method for constructing the cord.
Figure 7B:
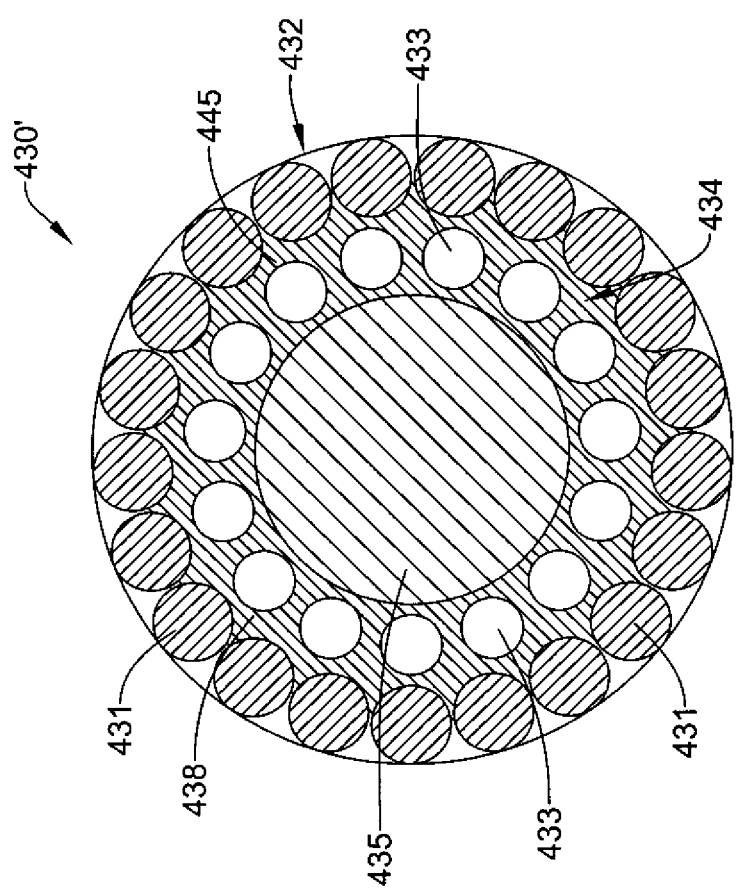

FIGS. 7A and 7B illustrate an alternative configuration of a cord 430 and method for constructing the cord 430. The cord 430 may include an outer layer 432 formed of a plurality of filaments 431 surrounding an inner layer 434 formed of a plurality of filaments 433 similar to that of the cord 30. The cord 430 may optionally also include a central core material 435 located within the inner layer 434. The core 435 may be similar in material, construction, and/or configuration to the core 35 discussed above.

The plurality of filaments 431 forming the outer layer 432 may be braided, woven, knitted, twisted or otherwise intermingled to form the outer layer 432 in some embodiments. Thus, in some embodiments the outer layer 432 may be a braided, woven, knitted, or twisted layer of the cord 430. Furthermore, the plurality of filaments 433 forming the inner layer 434 may be braided, woven, knitted, twisted or otherwise intermingled to form the inner layer 434 in some embodiments. Thus, in some embodiments the inner layer 434 may be a braided, woven, knitted, or twisted layer of the cord 430. The material of the filaments 431, 433 of the outer layer 432 and/or the inner layer 434 may be one of the materials listed above regarding possible materials of the filaments 33a, 33b, or another material if desired.

Prior to a manufacturing process in which the filaments 433 of the inner layer 434 are intermingled (e.g., braided, woven, knitted, twisted, etc.), the filaments 433 may be coated with an elastic material 445. For example, the filaments 433 may be coated with the elastic material 445 contemporaneously with formation of the filaments 433 through a co-extrusion process. In other embodiments, filaments 433 may subsequently be coated with the elastic material 445 by one of numerous deposition techniques such as spraying a melt or solution, or by coating the filaments 433 by dipping the filaments in a melt or solution of the elastic material 445.

After the filaments 433 have been coated with the elastic material 445, which may be more elastic that the material of the filaments 433, the filaments 433 may be intermingled (e.g., braided, woven, knitted, twisted, etc.) to form the inner layer 434.

The elastic material 445 coating the filaments 433 may subsequently be caused to flow by melting and/or dissolving the elastic material 445. In some embodiments, it may be desired to perform a combination of using solvents and/or elevated temperatures to manipulate the cord construct. For example, the cord 430 may be subjected to an elevated temperature and/or submerged in a solvent to melt and/or dissolve the elastic material 445 coating the filaments 433. The elastic material may then flow around the filaments 433 of the inner layer 434 and/or within the confines of the outer layer 432. The presence of the outer layer 432 may constrain the elastic material 445 within the confines of the outer layer 432, or another layer or sleeve may be placed over the cord 430 to constrain the elastic material 445. Subsequently, cooling the elastic material 445 and/or removing the solvent may consolidate and solidify the elastic material 445 into a solid elastic body 438.

The modified cord 430', shown in FIG. 7B results in the solid elastic body 438 of the elastic material 445 surrounding or encasing the filaments 433 of the inner layer 434. Thus, the filaments 433 of the inner layer 434 may be embedded (e.g., partially or fully embedded) in an elastic matrix of the elastic material of the solid elastic body 438.

The solid elastic body 438 may provide the cord 430' with a degree of elasticity, while the filaments 433 embedded in the solid elastic body 438 and/or the filaments 431 of the outer layer 432 may provide the cord 430' with a degree of rigidity or stiffness. Furthermore, the solid elastic body 438 may restrict decreases in braid angle during axial loading of the cord 430', providing a degree of rigidity or stiffness to the cord 430'. In one specific example, the filaments 433 of the inner layer 434 may be formed of polyethylene terephthalate (PET). Thus, the PET filaments 433 may be embedded in an elastic matrix of the elastic material of the solid elastic body 438.

Through an initial range of axial loading, the axial load may be transferred, at least primarily, through the inner layer 434, and through further ranges of axial loading the axial load may be reallocated between both the inner layer 434 and the outer layer 432. Thus, as the axial load is transferred to the outer layer 432, the stiffness of the cord 430' may increase. Thus, the inner layer 434 may dictate the stiffness of the cord 430' through a first range of displacement and/or axial loading of the cord 430', and the outer layer 432 may dictate the stiffness of the cord 430' through a second range of displacement and/or axial loading of the cord 430', greater than the first range of displacement and/or axial loading.

Figure 8A:
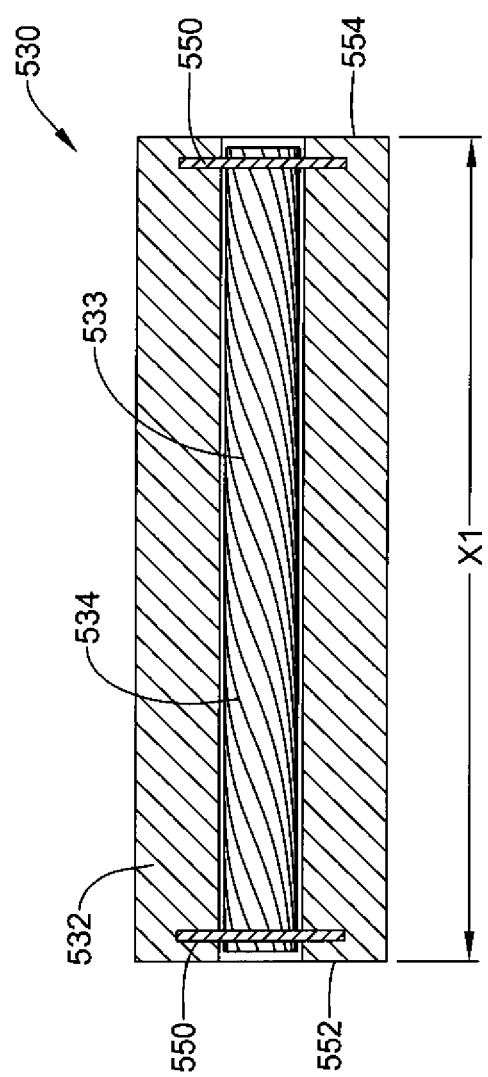
FIGS. 8A and 8B illustrate an alternative configuration of a cord for use in a vertebral stabilization system.
Figure 8B:
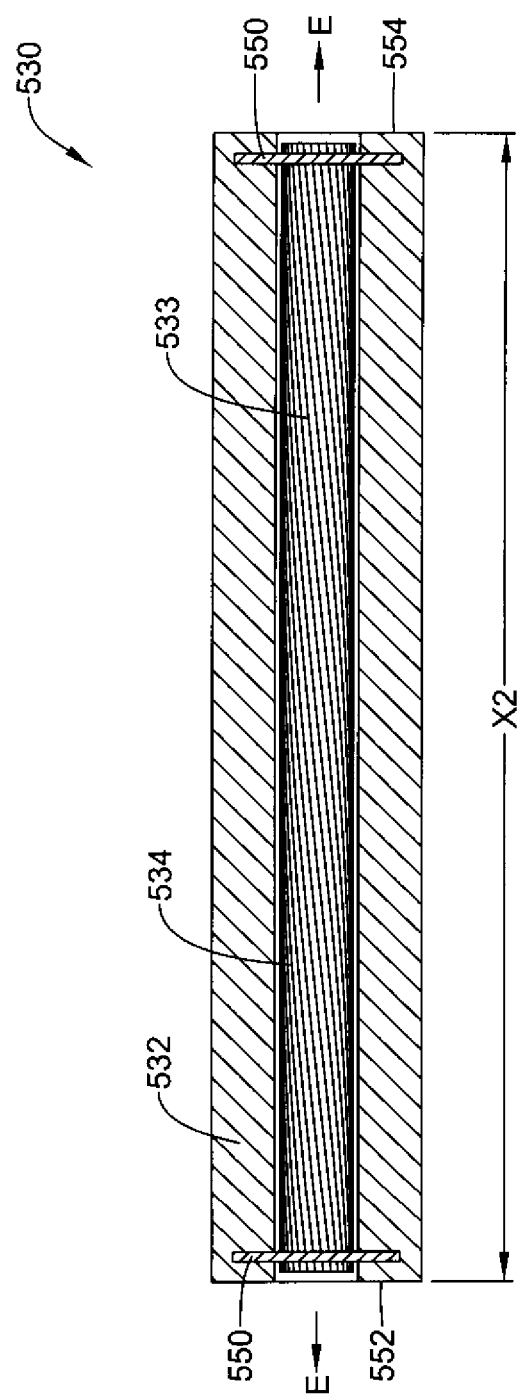

Another embodiment of a cord 530 is shown in FIGS. 8A and 8B. The cord 530 may include an outer layer 532 and an inner layer 534 extending through the outer layer 532. In some embodiments, the outer layer 532, disposed around the inner layer 534, may be a tubular member or construct having a lumen extending therethrough. For example, in some embodiments the outer layer 532 may be a tubular braided, woven or knitted member formed of one or more, or a plurality of intermingled filaments. In other embodiments, the outer layer 532 may be a tubular member formed of a unitary construction, such as a polymer tube. In some embodiments, such a tubular member may include one or more, or a plurality of cuts, notches, grooves, slits, slots, openings or other features providing desired flexibility characteristics to the tubular member. The outer layer 532 may be formed of an elastic material, such as an elastomeric polymer, including, but not limited to those polymers listed above having a desired elasticity.

The inner layer 534, located inside of the outer layer 532, may include one or more, or a plurality of loose fibers 533 extending through the outer layer 532. Although the embodiment shown in FIGS. 8A and 8B includes an inner layer 534 of a plurality of filaments 533, in some embodiments the inner layer 534 may be formed of a singular filament 533 if desired. In some embodiments, the filaments 533 may be coiled, twisted, braided, knitted, woven, or otherwise intermingled along the axis of the longitudinal axis of the cord 530. In other embodiments, the filaments 533 may be axially aligned and extend generally parallel to the longitudinal axis of the cord 530.

The end portions of the inner layer 534 may be secured to the outer layer 532, for example the end portions of the outer layer 532. For instance, a retention member 550, shown as an annular ring crimped around the inner layer 534 and imbedded in the outer layer 532, may be used to secure each of the end portions of the inner layer 534 to the outer layer 532. In other embodiments, a retention member 550 may be secured to each of the end portions of the inner layer 534 and be positioned in abutting contact with an end surface of the outer layer 532. For instance, a first retention member 550 may be secured to a first end portion of the inner layer 534 and be located exterior of and/or in abutting contact with a first end surface 552 of the outer layer 532, and a second retention member 550 may be secured to a second end portion of the inner layer 534 and be located exterior of and/or in abutting contact with a second end surface 554 of the outer layer 532. It is noted that others ways of securing the end portions of the inner layer 534 to the outer layer 532 are contemplated.

FIG. 8A illustrates the cord 530 in a first, relaxed non-elongated position in which the cord 530 is not subjected to an applied axial tensile loading. As can be seen from FIG. 8A, in the non-elongated position, the filaments of the inner layer 534 are positioned loosely within the outer layer 532 and not taut. In the relaxed, non-elongated position the cord 530 may have an axial length X1.

As an axial force E is applied to the end portions of the cord 530, as shown in FIG. 8B, the cord 530 is elongated. During an initial amount of elongation of the cord 530 (e.g., when the cord is subjected to a low amount of axial loading), the outer layer 532 may be axially loaded, and thus stretched and/or deformed. However, during this initial amount of elongation of the cord 530 the inner layer 534 is not axially loaded. At a threshold level of axial loading, the inner layer 534 becomes taut, at which point further axial loading of the cord 530 is distributed between the inner layer 534 and the outer layer 532. For instance, as shown in FIG. 8B, at a threshold level of elongation X2, the inner layer 534 becomes taut. Thus, further elongation of the cord 530, by increasing the tensile force E applied to the cord 530, would result in the tensile force E being distributed between the inner layer 534 and the outer layer 532. When the inner layer 534 becomes taut, the cord 530 may experience an increase of stiffness.

Therefore, the cord 530 may have a first stiffness throughout a first range of elongation from a relaxed, non-elongated length X1 to a threshold amount of elongation at an elongated length X2. When the cord 530 is further elongated through a second range of elongation greater than the threshold amount of elongation (i.e., has an elongated length greater than X2), the cord 530 may have a second stiffness greater than the first stiffness of the cord 530. In other words, the cord 530 effectively has "slack" built into its construction which is tightened or drawn taut when the cord 530 reaches and/or surpasses a threshold amount of elongation (e.g., when the cord 530 is axially loaded beyond a threshold amount of axial loading).

Figure 9A:
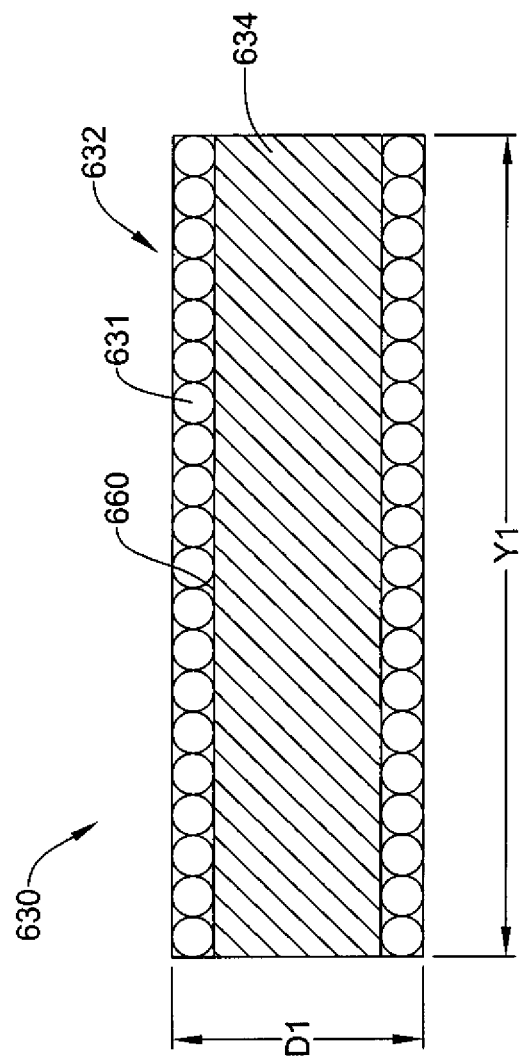
FIGS. 9A and 9B illustrate an alternative configuration of a cord for use in a vertebral stabilization system.
Figure 9B:
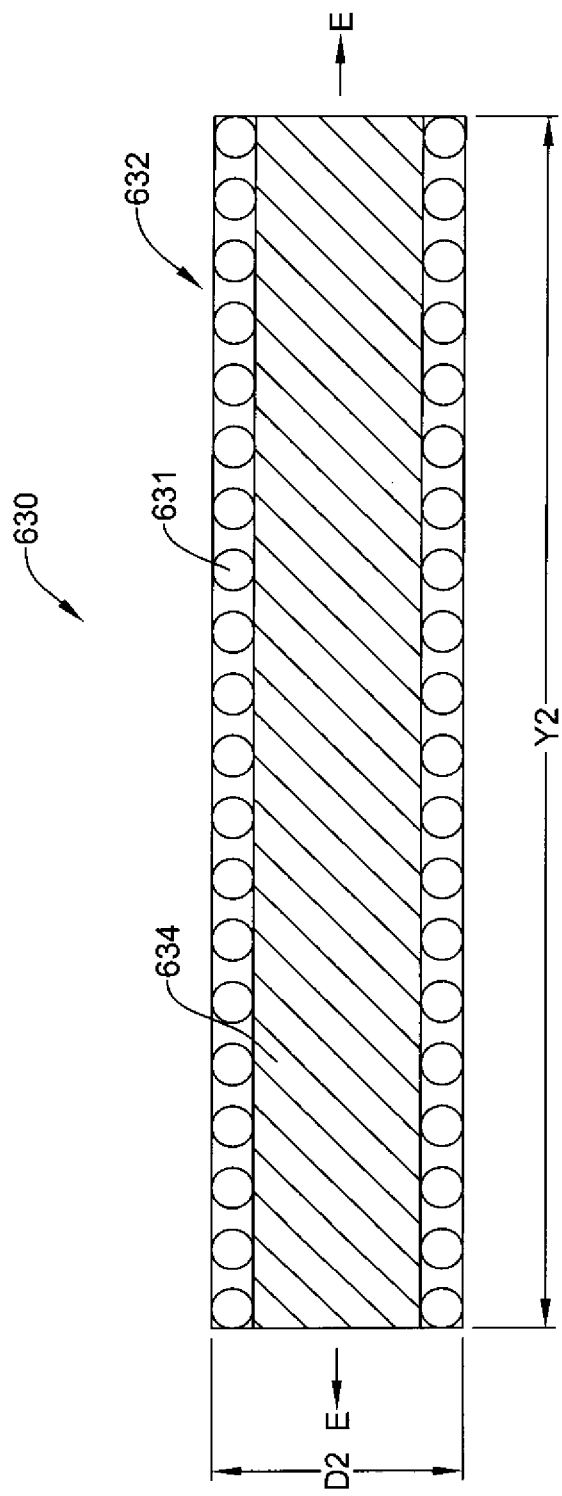

Another embodiment of a cord 630 is illustrated in FIGS. 9A and 9B. The cord 630 may include an outer layer 632 and an inner layer 634 extending through the outer layer 632. In some embodiments, the outer layer 632, disposed around the inner layer 634, may be a tubular braided, woven or knitted member formed of one or more, or a plurality of intermingled filaments 631. The filaments 631 of the outer layer 632 may be formed of any desired material, including those materials listed above with regard to the filaments 31, 33a, 33b. For instance, in some embodiments, the outer layer 632 may be a braided layer formed of a plurality of braided filaments made of polyethylene terephthalate (PET).

The inner layer 634, which may extend through at least a portion of the length of the outer layer 632 may be an elastically compressible body formed of an elastic material, such as one of the elastic materials disclosed above.

The outer layer 632 may be positioned over the inner layer 634, defining an interface 660 therebetween. The outer layer 632 may be located adjacent to, but not bonded to the inner layer 634 at the interface 660. In some embodiments, the outer layer 632 may be loosely positioned over the inner layer 634 such that there is a gap or space between the outer layer 632 and the inner layer 634. The gap or space at the interface 660 has been exaggerated in FIG. 9A for illustrative purposes.

As shown in FIG. 9A, when the cord 630 is in a non-elongated configuration, the cord 630 may have a length Y1 and the outer layer 632 may have an outer diameter D1. As the cord 630 is axially loaded with a tensile force E, shown in FIG. 9B, and elongates to an elongated length Y2, the outer layer 632 undergoes a decrease in outer diameter to an outer diameter D2, at which point the outer layer 632 compresses against the outer surface of the inner layer 634. Further elongation of the cord 630 is restricted as the presence of the inner layer 634 restricts a further decrease in diameter of the outer layer 632, and thus restricts further elongation of the outer layer 632. Therefore, in order to achieve further elongation of the cord 630, the inner layer 634 must be compressed radially inward by the reduction in diameter of the outer layer 634, resulting in a change in stiffness of the cord 630.

In such an embodiment, the cord 630 may have a first stiffness throughout a first range of displacement from a non-elongated length Y1 to a threshold amount of displacement at an elongated length Y2. Through the first range of displacement, the outer layer 632 is axially loaded. When the cord 630 is further displaced through a second range of displacement greater than the threshold amount of displacement (i.e., has an elongated length greater than Y2), the cord 630 may have a second stiffness greater than the first stiffness of the cord 630. Through the second range of displacement, both the outer layer 632 and the inner layer 634 are axially loaded. In other words, through a first range of axial loading up to a threshold level of tensile force, the cord 630 has a first stiffness, and through a second range of axial loading greater than the threshold level of tensile force, the cord 630 has a second stiffness greater than the first stiffness.

Figure 10A:
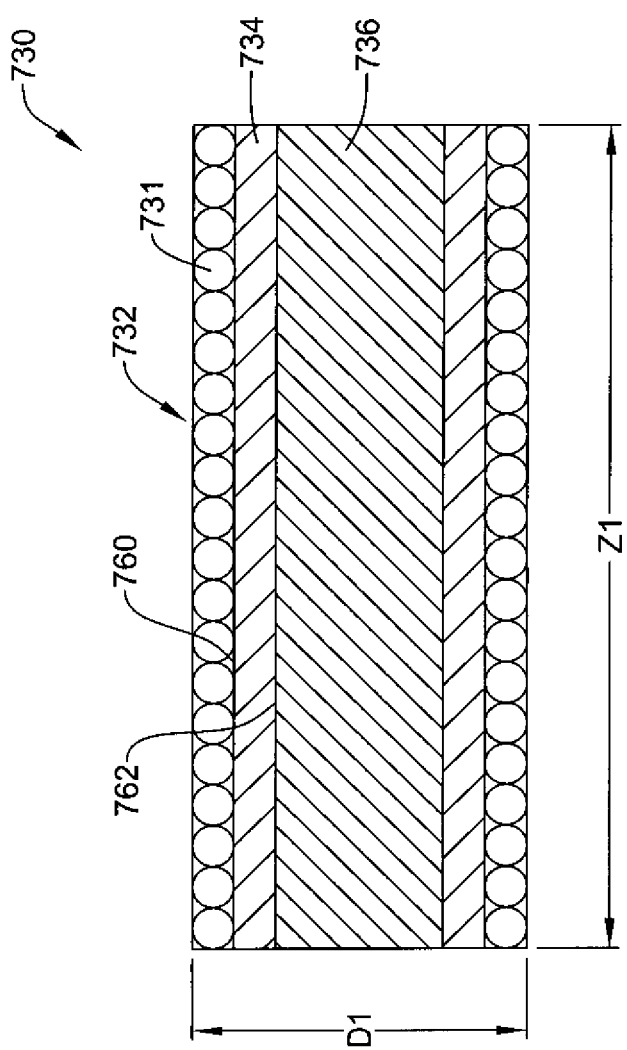
FIGS. 10A, 10B and 10C illustrate an alternative configuration of a cord for use in a vertebral stabilization system.
Figure 10B:
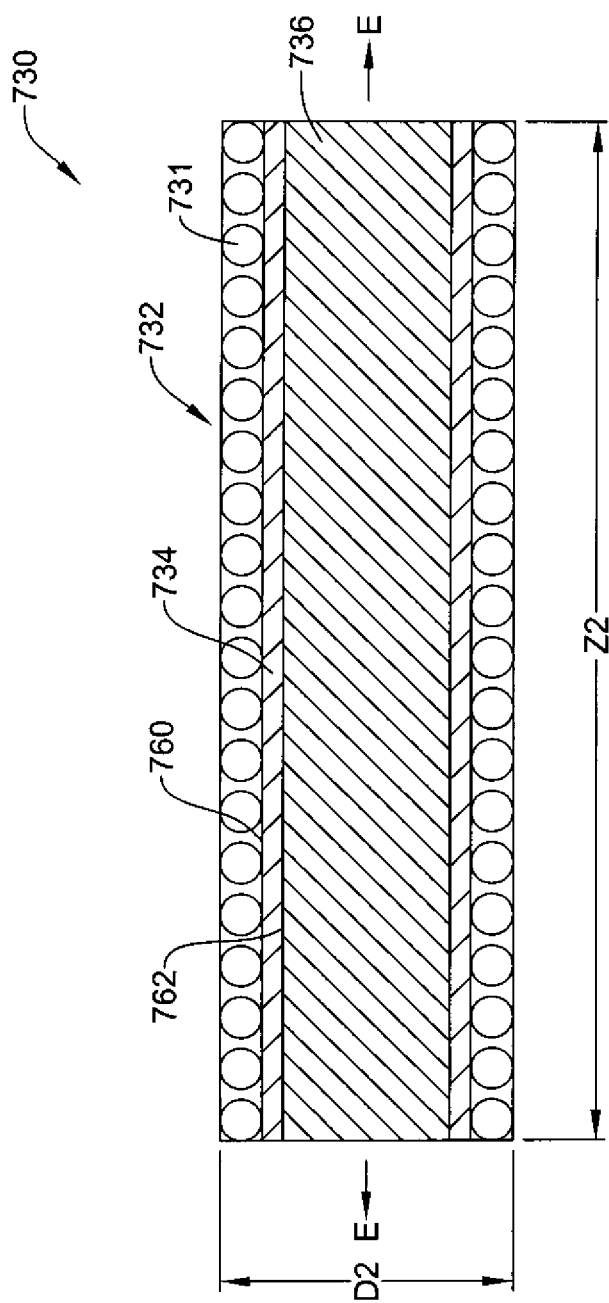

Another embodiment of a cord 730, similar to the cord 630, is illustrated in FIGS. 10A and 10B. The cord 730 may include an outer layer 732, a first elastic component 734 extending through the outer layer 732, and a second elastic component 736 extending through the first elastic component 734. In some embodiments, the outer layer 732, disposed around the first elastic component 734, may be a tubular braided, woven or knitted member formed of one or more, or a plurality of intermingled filaments 731. The filaments 731 of the outer layer 732 may be formed of any desired material, including those materials listed above with regard to the filaments 31, 33a, 33b. For instance, in some embodiments, the outer layer 732 may be a braided layer formed of a plurality of braided filaments made of polyethylene terephthalate (PET).

The first elastic component 734, which may extend through at least a portion of the length of the outer layer 732 may be an elastically compressible body formed of an elastic material having a first elasticity, such as one of the elastic materials disclosed above.

Additionally, the second elastic component 736, which may extend through at least a portion of the length of the first elastic component 734, may be an elastically compressible body formed of an elastic material having a second elasticity, such as one of the elastic materials disclosed above. In some embodiments, the stiffness of the second elastic component 736 may be greater than the stiffness of the first elastic component 734.

The outer layer 732 may be positioned over the first elastic component 734, defining an interface 760 therebetween. The outer layer 732 may be located adjacent to, but not bonded to the first elastic component 734 at the interface 760. In some embodiments, the outer layer 732 may be loosely positioned over the first elastic component 734 such that there is a gap or space between the outer layer 732 and the first elastic component 734. The gap or space at the interface 760 has been exaggerated in FIG. 10A for illustrative purposes.

The first elastic component 734 may be positioned over the second elastic component 736, defining an interface 762 therebetween. The first elastic component 734 may be located adjacent to, but not bonded to the second elastic component 736 at the interface 762. In some embodiments, the first elastic component 734 may be loosely positioned over the second elastic component 736 such that there is a gap or space between the first elastic component 734 and the second elastic component 736. The gap or space at the interface 762 has been exaggerated in FIG. 10A for illustrative purposes.

As shown in FIG. 10A, when the cord 730 is in a non-elongated configuration, the cord 730 may have a length Z1 and the outer layer 732 may have an outer diameter D1. As the cord 730 is axially loaded with a tensile force E1, shown in FIG. 10B, and elongates to an elongated length Z2, the outer layer 732 undergoes a decrease in outer diameter to an outer diameter D2, at which point the outer layer 732 compresses against the outer surface of the first elastic component 734. Further elongation of the cord 730 is restricted as the presence of the first elastic component 734 restricts a further decrease in diameter of the outer layer 732, and thus restricts further elongation of the outer layer 732. Therefore, in order to achieve further elongation of the cord 730, the first elastic component 734 must be compressed radially inward by the reduction in diameter of the outer layer 734, resulting in a change in stiffness of the cord 730.

Figure 10C:
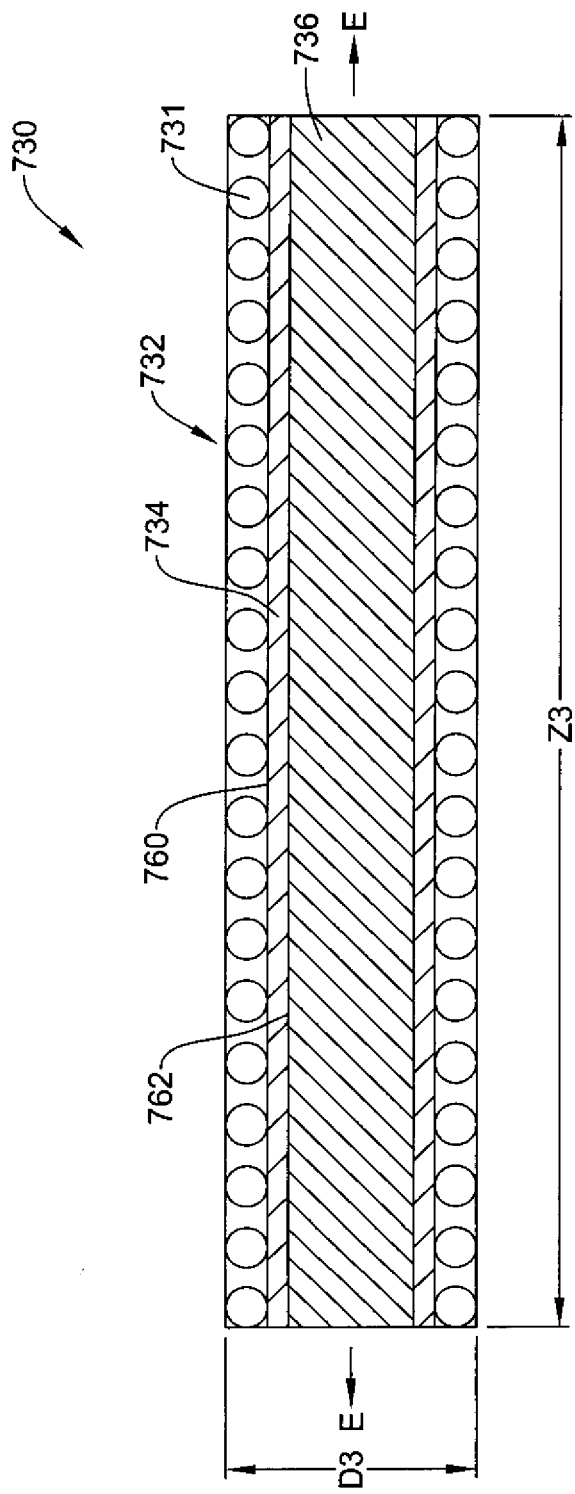

As the cord 730 is further axially loaded with a tensile force E2 greater than the tensile force E1, shown in FIG. 10C, and elongates to an elongated length Z3, the diameter of the cord 730 will decrease further to a diameter D3, at which point the first elastic component 734 compresses radially inward against the outer surface of the second elastic component 736. Further elongation of the cord 730 is restricted as the presence of the second elastic component 736 restricts radial compression of the first elastic component 734 and a further decrease in diameter of the outer layer 732, and thus restricts further elongation of the cord 730. Therefore, in order to achieve further elongation of the cord 730, the second elastic component 736 must be compressed radially inward by the first elastic component 734, resulting in a change in stiffness of the cord 730.

In such an embodiment, the cord 730 may have a first stiffness throughout a first range of displacement from a non-elongated length Z1 to a first amount of displacement at an elongated length Z2. Through the first range of displacement, the outer layer 732 is axially loaded. When the cord 730 is further elongated through a second range of displacement greater than the first range of displacement (i.e., has an elongated length greater than Z2 but less than Z3), the cord 730 may have a second stiffness greater than the first stiffness of the cord 730. Through the second range of displacement, both the outer layer 732 and the first elastic component 734 are axially loaded. When the cord 730 is further elongated through a third range of displacement greater than the second range of displacement (i.e., has an elongated length greater than Z3), the cord 730 may have a third stiffness greater than the second stiffness of the cord 730. In other words, through a first range of axial loading up to a first threshold level of tensile force, the cord 730 has a first stiffness, through a second range of axial loading greater than the first threshold level of tensile force but less than a second threshold level of tensile force, the cord 730 has a second stiffness greater than the first stiffness, and through a third range of axial loading greater than the second threshold level of tensile force, the cord 730 has a third stiffness greater than the second stiffness.

Figure 11:
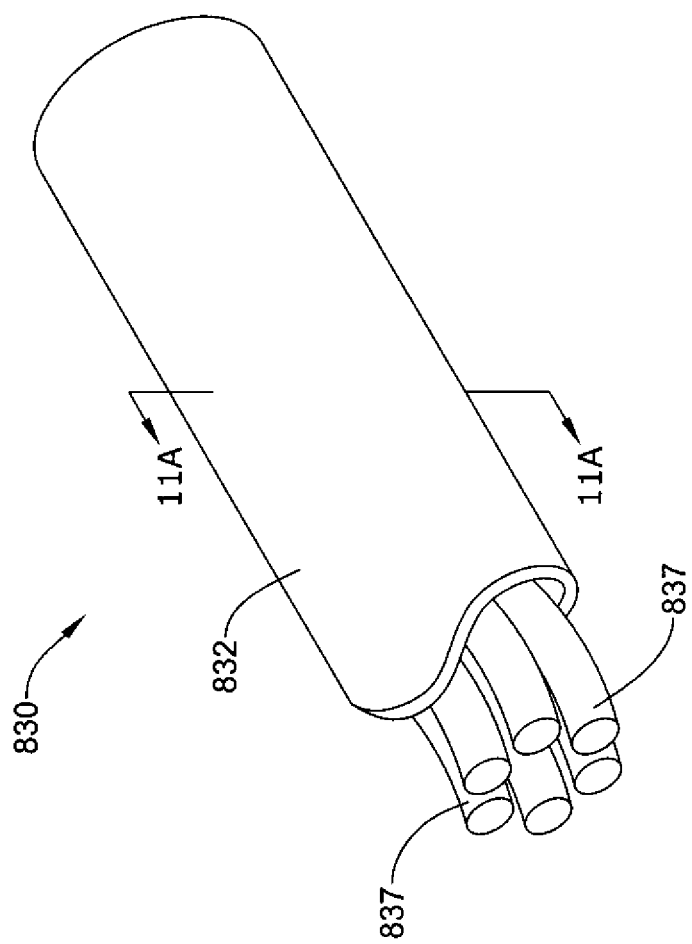
FIGS. 11, 11A and 11B illustrate an alternative configuration of a cord for use in a vertebral stabilization system.
Figure 11B:
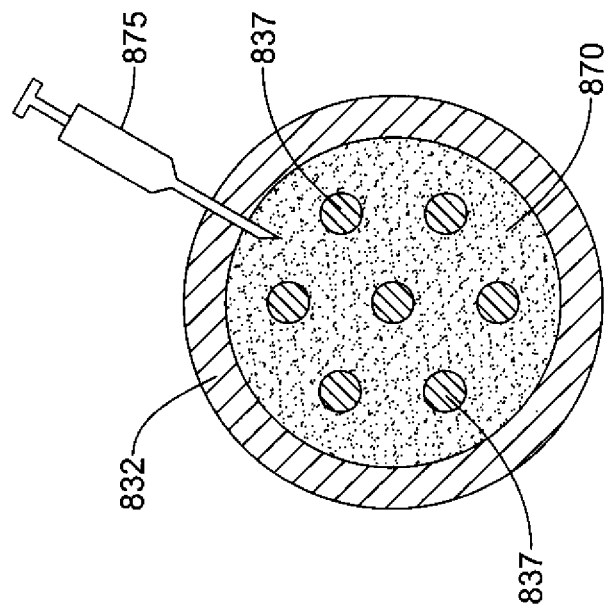
Figure 11A:
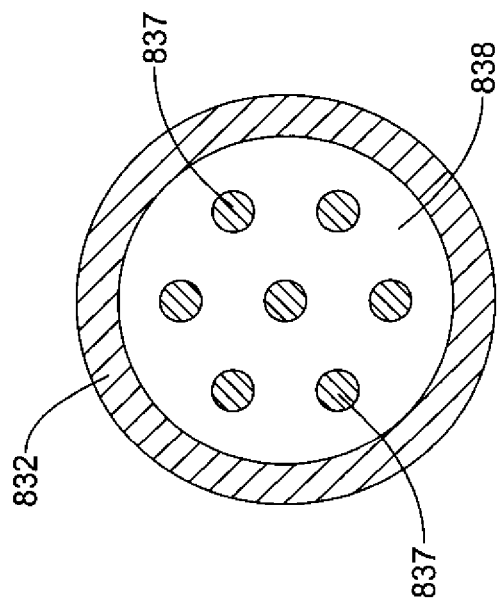

Another cord 830 and method of constructing the cord 830 is illustrated in FIGS. 11, 11A and 11B. The cord 830 may be a structure constructed in situ during a medical procedure. For example, the cord 830 may include an outer layer 832 surrounding one or more, or a plurality of filaments 837. The filaments 837 may be formed of any desired material, including those materials mentioned above regarding the filaments 31, 33a, and 33b. As the volume of the filaments 837 may not fill the entire space of the lumen of the outer layer 832, a void space 838 may remain within the outer layer 832, as shown in FIG. 11A. In some embodiments, the outer layer 832 may have a smooth outer surface, while in other embodiments the outer layer 832 may have an irregular or roughened outer surface.

The cord 830 may be placed in a desired location in a patient during a medical procedure. For example, the cord 830 may be extended between a first vertebral anchor and a second vertebral anchor in some embodiments. As shown in FIG. 11B, once the cord 830 is positioned in the patient's body, a material 870 may be injected or otherwise introduced into the void space 838 to surround the filaments 837. For example, the material 838 may be injected into the void space with an applicator 875, such as a syringe or other application device. In some embodiments, the material 838 may be a solution including an elastic material or the material 838 may be a liquid monomer.

Once introduced around the filaments 837, the material may then be cured into an elastic matrix in situ by the action of heat, ultraviolet (UV), chemical, or other curing initiators. Thus, the elastic material may be polymerized around the filaments 837 in situ to form an elastic body having the filaments 837 imbedded therein. In some embodiments, the outer layer 832 may be removed from the remaining structure of the cord 830 once the elastic body is formed and cured around the filaments 437. For example, in some embodiments the outer layer 832 may be a thin film which may be peeled away from the elastic body surrounding the filaments 837. In other embodiments, the outer layer 832, which may be a film, sleeve, jacket, or other layer, may remain a component of the cord 830 upon completion of the installation of a vertebral stabilization system. In still other embodiments, the outer layer 832, may be a biodegradable and/or bioabsorbable polymer which resorbs over time, in situ.

The material 838 may be chosen for its elasticity and/or the filaments 837 may be chosen for their stiffness in the construction of the cord 830. Thus, by selecting desired materials for the curing material 838, filaments and/or the outer layer 832, the cord 830 may be constructed to have a desired stiffness, such as a variable stiffness over a range of displacement and/or loading.

Figure 12A:
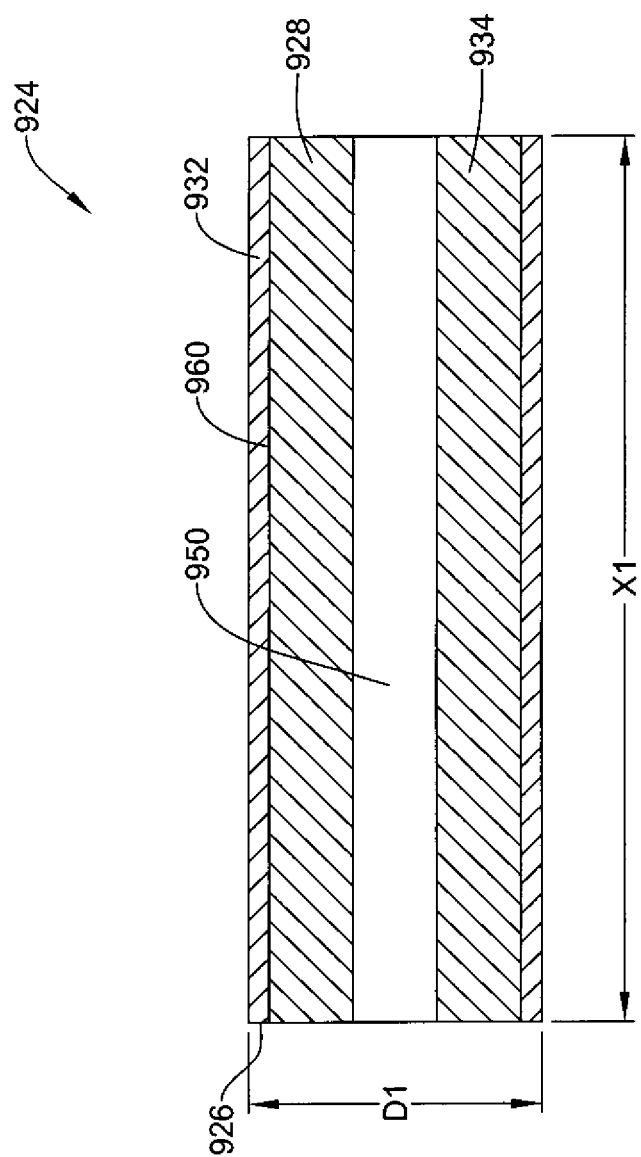
FIGS. 12A and 12B illustrate an alternative configuration of a spacer for use in a vertebral stabilization system.
Figure 12B:
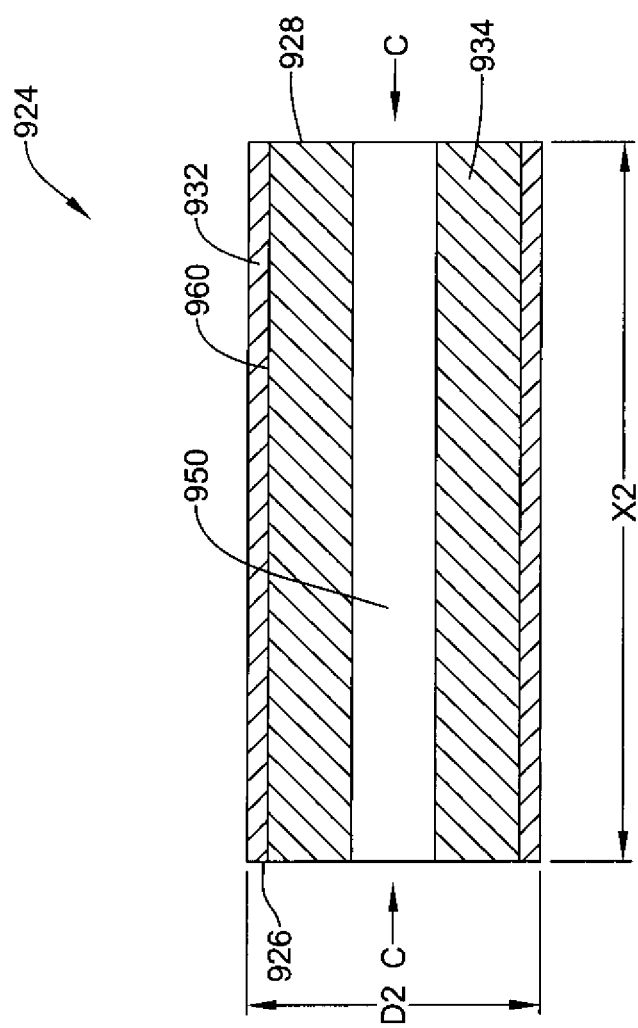

Other desirable characteristics of the vertebral stabilization system 10, shown in FIG. 1, may be achieved by incorporating a spacer 924, shown in FIGS. 12A and 12B, with the vertebral stabilization system 10. The spacer 924 may include an outer layer or jacket 932 and an inner layer 934. The inner layer 934 may include a lumen 950 extending therethrough from a first end 926 to a second end 928 of the spacer 924. Each of the outer layer 932 and the inner layer 934 may be formed of any desired material, including those listed above regarding the filaments 31, 33a, 33b. For instance, the inner layer 934 may be formed of an elastic material having a first elasticity and the outer layer 932 may be formed of a more inelastic material, such as a rigid or semi-rigid material, having a second elasticity less than the elasticity of the inner layer 934. In some embodiments, the outer layer 932 may have a smooth outer surface, while in other embodiments the outer layer 932 may have an irregular or roughened outer surface.

In some embodiments, the outer layer 932 may include a filled or reinforced polymer having one or more, or a plurality of filaments combined with a polymer matrix to form the outer layer 932. For instance, in some embodiments the outer layer 932 may be filled with carbon, glassy, metallic, ceramic or polymeric inclusions with macro-, micro-, or nanoscale dimensions and may be discontinuous or continuous fiber, ribbon, needle, ellipsoid, cylindrical, platelet, disk, spherical, cubic, regular or irregular geometries, or a combination thereof, in a range of volume fractions and size distributions. These particles may be biostable or biodegradable in situ. The incorporation of these particles may contribute to mechanical performance, biological performance, remote detection (e.g., radiopacity), degradation resistance or acceleration, delivery of a drug, therapeutic agent, or other active ingredient, or a combination thereof.

The outer layer 932 may be positioned over the inner layer 934, defining an interface 960 therebetween. The outer layer 932 may be located adjacent to, but not bonded to the inner layer 934 at the interface 960. In some embodiments, the outer layer 932 may be loosely positioned over the inner layer 934 such that there is a gap or space between the outer layer 932 and the inner layer 934. The gap or space at the interface 960 has been exaggerated in FIG. 12A for illustrative purposes.

As shown in FIG. 12A, when the spacer 924 is in a non-compressed configuration, the spacer 924 may have a length X1 and may have an outer diameter D1. As the spacer 924 is axially loaded with a compressive force C, shown in FIG. 12B, and is compressed to compressed length X2, the inner layer 934 radially expands, at which point the inner layer 934 compresses against the inner surface of the outer layer 932. Further compression of the spacer 924 is restricted as the presence of the outer layer 932 restricts a further increase in diameter of the inner layer 934, and thus restricts further compression of the spacer 924. Therefore, in order to achieve further compression of the spacer 924, a greater compressive force is necessary to overcome the restrictive nature of the outer layer 932, resulting in a change in stiffness of the spacer 924.

In such an embodiment, the spacer 924 may have a first stiffness throughout a first range of compression from a non-compressed length X1 to a threshold amount of compression at a compressed length X2. Through the first range of compression, the inner layer 932 is axially loaded in compression. When the spacer 924 is further compressed through a second range of compression greater than the threshold amount of compression (i.e., has a compressed length less than X2), the spacer 924 may have a second stiffness greater than the first stiffness of the spacer 924. Through the second range of compression, both the outer layer 932 and the inner layer 934 are axially loaded in compression. In other words, through a first range of axial loading up to a threshold level of compressive force, the spacer 924 has a first stiffness, and through a second range of axial loading greater than the threshold level of compressive force, the spacer 924 has a second stiffness greater than the first stiffness.

Although the cord designs discussed herein have been illustrated with a circular cross-section, it is noted that in some embodiments it may be possible and/or desirable to provide the cord designs with a non-circular cross-section. For instance, tape, ribbon, rectangular, triangular, elliptical, as well as other regular or irregular cross-sectional geometries are possible.

Those skilled in the art will recognize that the present invention may be manifested in a variety of forms other than the specific embodiments described and contemplated herein. For example, technologies described herein may be directed to various animal species, not necessarily limited to humans. Additionally, although technologies described herein have been discussed in regard to the spinal column, it is understood that they may also be applied in other medical applications, if desired. For example, it may be found advantageous to utilize a cord as described herein for tendon replacement, or other desired applications. Accordingly, departure in form and detail may be made without departing from the scope and spirit of the present invention as described in the appended claims.

What is claimed is:

1. A dynamic stabilization system for stabilizing a vertebral segment of a spine, the system comprising:
    a first vertebral anchor configured to be secured to a first vertebra;
    a second vertebral anchor configured to be secured to a second vertebra;
    a cord extendable from the first vertebral anchor to the second vertebral anchor, the cord having a variable stiffness through a range of displacement; and
    a spacer surrounding a portion of the cord;
    wherein:
    the stiffness of the cord increases as an applied tensile force on the cord is increased;
    the cord has a first phase of stiffness through a first range of displacement, a second phase of stiffness through a second range of displacement, and a third phase of stiffness through a third range of displacement; and
    the stiffness in the cord in the first phase is less than the stiffness in the cord in the third phase, and the stiffness of the cord in the second phase progressively increases from the stiffness in the cord in the first phase to the stiffness in the cord in the third phase.

2. The dynamic stabilization system of claim 1, wherein the second phase of stiffness is in the range of about 100 N/mm to about 250 N/mm.

3. The dynamic stabilization system of claim 1, wherein the first phase of stiffness is in the range of about 0 N/mm to about 100 N/mm and the third phase of stiffness is greater than about 200 N/mm.

4. The dynamic stabilization system of claim 1, wherein the cord includes a plurality of filaments, wherein a first subset of the plurality of filaments have a first tensile modulus of elasticity of more than 1 GPa and a second subset of the plurality of filaments have a second tensile modulus of elasticity of less than 1 GPa.

5. The dynamic stabilization system of claim 4, wherein the first subset of filaments are intermingled with the second subset of filaments.

6. The dynamic stabilization system of claim 4, wherein the first subset of filaments are located in an outer braided layer of the cord, and the second subset of filaments are located in an inner braided layer of the cord.

7. The dynamic stabilization system of claim 1, wherein the spacer includes a lumen, and the cord is sized for insertion through the lumen of the spacer.

8. A dynamic stabilization system for stabilizing a vertebral segment of a spine, the system comprising:
    a first vertebral anchor configured to be secured to a first vertebra;
    a second vertebral anchor configured to be secured to a second vertebra;
    a spacer positionable between the first vertebral anchor and the second vertebral anchor; and
    a cord sized for insertion through the spacer;
    wherein the cord includes a means for varying the stiffness of the cord dependent of a tensile load applied to the cord;
    further wherein the dynamic stabilization system is capable of being configured when implanted in a patient such that the cord is placed in tension and the spacer is placed in compression between the first and second vertebral anchors.

9. The dynamic stabilization system of claim 8, wherein the cord includes a first plurality of filaments having a first elasticity intermingled with a second plurality of filaments having a second elasticity less than the first elasticity.

10. The dynamic stabilization system of claim 9, wherein the first plurality of filaments and the second plurality of filaments are included in an inner braided member; and
    wherein the cord further includes an outer braided member surrounding the inner braided member.

11. The dynamic stabilization system of claim 10, wherein the outer braided member includes a third plurality of filaments having a third elasticity less than the first elasticity.

12. The dynamic stabilization system of claim 8, wherein the cord includes:
    an elastic component having a first elasticity;
    a plurality of filaments imbedded in the elastic component; and
    an outer braided layer surrounding the elastic component;
    wherein the plurality of filaments have a second elasticity less than the first elasticity.

13. The dynamic stabilization system of claim 8, wherein the cord includes a collection of fibers extending through an outer member;
- wherein through a first range of displacement of the cord the collection of fibers are not drawn taut; and
- wherein through a second range of displacement of the cord the collection of fibers are drawn taut.

14. The dynamic stabilization system of claim 8, wherein the cord includes an outer braided layer surrounding an elastically compressible body;
- wherein through a first range of displacement of the cord an inner diameter of the outer braided layer is reduced; and
- wherein through a second range of displacement of the cord the inner diameter of the outer braided layer is restricted from being reduced by the presence of the elastically compressible body.

* * * * *